United States Patent
Besch et al.

(10) Patent No.: US 11,216,567 B2
(45) Date of Patent: Jan. 4, 2022

(54) DEFINING PRIVILEGES IN ASSOCIATION WITH THE AUTOMATED CONFIGURATION, IMPLEMENTATION AND/OR MAINTENANCE OF A HEALTHCARE INFORMATION SYSTEM

(71) Applicant: CERNER INNOVATION, INC., Kansas City, KS (US)

(72) Inventors: Jennifer L. Besch, Prairie Village, KS (US); Theresa M. Wavada, Kansas City, MO (US); Megan Barbre, Leawood, KS (US); Sara J. Charlson, Smithville, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 962 days.

(21) Appl. No.: 15/678,955

(22) Filed: Aug. 16, 2017

(65) Prior Publication Data
US 2018/0025457 A1  Jan. 25, 2018

Related U.S. Application Data

(63) Continuation of application No. 11/765,221, filed on Jun. 19, 2007, now abandoned.
(Continued)

(51) Int. Cl.
*G06F 21/60* (2013.01)
*G06F 21/62* (2013.01)
(Continued)

(52) U.S. Cl.
CPC ........ *G06F 21/604* (2013.01); *G06F 21/6245* (2013.01); *G06Q 10/10* (2013.01);
(Continued)

(58) Field of Classification Search
CPC ........ G06Q 50/24; G06Q 10/10; G16H 10/60; G16H 40/67; G16H 40/20
(Continued)

(56) References Cited

U.S. PATENT DOCUMENTS 4,878,175 A  10/1989  Norden-Paul et al.
5,321,610 A * 6/1994  Breslin ................ G06Q 10/10
                                                    705/7.17
(Continued)

FOREIGN PATENT DOCUMENTS

EP  1724681 A1 * 11/2006  ............... G06F 8/61

OTHER PUBLICATIONS

Columbus, Suzanne. "Small Practice, Big Decision: Selecting an EHR System for Small Physician Practices" Journal of AHIMA 77, No. 5 (May 2006): 42-46. (Year: 2006).*
(Continued)

*Primary Examiner* — Devin C Hein
(74) *Attorney, Agent, or Firm* — Shook, Hardy & Bacon L.L.P.

(57) ABSTRACT

Systems, methods and computer-readable media having computer-executable instructions embodied thereon, for automated configuration, implementation and/or maintenance of a healthcare information system are provided. The systems, methods and computer-readable media of embodiments described herein utilize a number of information sources prior to initiation of configuration, implementation and/or maintenance to tailor or flex the process in a manner that is facility- and/or personnel-specific, thus alleviating solicitation of unnecessary information. Such information sources may include, by way of example only, one or more of facility- and/or personnel-specific content, facility and personnel profiles, site profiles, help and knowledge assistance information, and pre-configured content options. The
(Continued)

more information to which the system has access prior to initiation of the configuration, implementation and/or maintenance process, the more tailored the configuration, implementation and/or maintenance may be and, accordingly, the less time and effort will be required by a user.

17 Claims, 30 Drawing Sheets

Related U.S. Application Data

(60) Provisional application No. 60/805,169, filed on Jun. 19, 2006.

(51) Int. Cl.
    *G06Q 10/10*     (2012.01)
    *G16H 10/60*     (2018.01)
    *G16H 40/20*     (2018.01)
    *G16H 40/67*     (2018.01)

(52) U.S. Cl.
    CPC ............. *G16H 10/60* (2018.01); *G16H 40/20* (2018.01); *G16H 40/67* (2018.01); *G06F 2221/2141* (2013.01); *G06F 2221/2149* (2013.01)

(58) Field of Classification Search
    USPC .......................................................... 705/2
    See application file for complete search history.

(56) References Cited

U.S. PATENT DOCUMENTS

| | | | |
|---|---|---|---|
| 5,881,225 | A | 3/1999 | Worth |
| 5,911,143 | A | 6/1999 | Deinhart et al. |
| 5,960,085 | A | 9/1999 | De La Huerga |
| 6,014,666 | A | 1/2000 | Helland et al. |
| 6,023,765 | A | 2/2000 | Kuhn |
| 6,032,119 | A | 2/2000 | Brown et al. |
| 6,047,259 | A | 4/2000 | Campbell et al. |
| 6,122,741 | A | 9/2000 | Patterson et al. |
| 6,161,126 | A | 12/2000 | Wies et al. |
| 6,161,139 | A | 12/2000 | Win et al. |
| 6,259,448 | B1 | 7/2001 | McNally et al. |
| 6,266,675 | B1 | 7/2001 | Evans et al. |
| 6,327,618 | B1 | 12/2001 | Ahlstrom et al. |
| 6,505,170 | B1 | 1/2003 | Seifert et al. |
| 6,574,736 | B1 | 6/2003 | Andrews |
| 6,684,188 | B1* | 1/2004 | Mitchell ............... G06F 40/174 705/3 |
| 6,714,913 | B2 | 3/2004 | Brandt et al. |
| 6,725,232 | B2 | 4/2004 | Bradley et al. |
| 6,727,921 | B1 | 4/2004 | Valad |
| 6,785,822 | B1 | 8/2004 | Sadhwani-Tully |
| 6,834,285 | B1* | 12/2004 | Boris ..................... G06Q 10/10 |
| 6,879,959 | B1 | 4/2005 | Chapman et al. |
| 6,912,710 | B2 | 6/2005 | Broussard et al. |
| 6,976,023 | B2 | 12/2005 | Chen et al. |
| 6,990,491 | B2 | 1/2006 | Dutta et al. |
| 7,085,834 | B2 | 8/2006 | Delany et al. |
| 7,103,874 | B2 | 9/2006 | McCollum et al. |
| 7,120,635 | B2 | 10/2006 | Bhide et al. |
| 7,185,192 | B1 | 2/2007 | Kahn |
| 7,219,234 | B1 | 5/2007 | Ashland et al. |
| 7,380,120 | B1 | 5/2008 | Garcia |
| 7,451,103 | B1 | 11/2008 | Boyle et al. |
| 7,519,169 | B1 | 4/2009 | Hingoranee et al. |
| 7,568,108 | B2 | 7/2009 | Monaco et al. |
| 7,640,429 | B2 | 12/2009 | Huang et al. |
| 7,644,008 | B1 | 1/2010 | Issa et al. |
| 7,650,644 | B2 | 1/2010 | Cheng et al. |
| 7,673,139 | B1 | 3/2010 | Satish et al. |
| 7,685,632 | B2 | 3/2010 | Vayman |
| 7,771,386 | B2 | 8/2010 | Eggers et al. |
| 7,937,655 | B2 | 5/2011 | Teng et al. |
| 8,000,977 | B2 | 8/2011 | Achan |
| 8,065,331 | B2 | 11/2011 | Muller et al. |
| 8,255,818 | B2 | 8/2012 | Bales et al. |
| 8,473,321 | B2 | 6/2013 | Astle et al. |
| 8,560,709 | B1 | 10/2013 | Shokhor et al. |
| 8,655,832 | B2 | 2/2014 | Muller et al. |
| 2002/0010679 | A1 | 1/2002 | Felsher |
| 2002/0026592 | A1 | 2/2002 | Gavrila et al. |
| 2002/0032582 | A1 | 3/2002 | Feeney et al. |
| 2002/0095499 | A1 | 7/2002 | Barnett et al. |
| 2002/0099568 | A1 | 7/2002 | Turner et al. |
| 2002/0099571 | A1 | 7/2002 | Waku et al. |
| 2002/0144142 | A1 | 10/2002 | Shohat |
| 2002/0158898 | A1 | 10/2002 | Hsieh et al. |
| 2002/0178119 | A1 | 11/2002 | Griffin et al. |
| 2003/0004754 | A1 | 1/2003 | Krutz |
| 2003/0023461 | A1 | 1/2003 | Quintanilla et al. |
| 2003/0074222 | A1 | 4/2003 | Rosow et al. |
| 2003/0078807 | A1 | 4/2003 | Cole et al. |
| 2003/0120515 | A1 | 6/2003 | Geller |
| 2003/0130866 | A1 | 7/2003 | Turner et al. |
| 2003/0140043 | A1 | 7/2003 | Hotchkiss et al. |
| 2003/0177412 | A1 | 9/2003 | Todd |
| 2004/0054663 | A1 | 3/2004 | Goodwin |
| 2004/0249674 | A1 | 12/2004 | Eisenberg et al. |
| 2005/0015775 | A1 | 1/2005 | Russell et al. |
| 2005/0021977 | A1 | 1/2005 | Oberst |
| 2005/0060397 | A1 | 3/2005 | Barthram et al. |
| 2005/0097440 | A1 | 5/2005 | Lusk et al. |
| 2005/0203771 | A1 | 9/2005 | Achan |
| 2006/0004588 | A1 | 1/2006 | Ananda |
| 2006/0017969 | A1 | 1/2006 | Ly et al. |
| 2006/0031094 | A1 | 2/2006 | Cohen et al. |
| 2006/0053035 | A1 | 3/2006 | Eisenberg |
| 2006/0074711 | A1 | 4/2006 | Mahesh et al. |
| 2006/0111749 | A1 | 5/2006 | Westenskow et al. |
| 2006/0123414 | A1* | 6/2006 | Fors ..................... G06F 8/61 717/177 |
| 2006/0156020 | A1 | 7/2006 | Minium et al. |
| 2006/0218394 | A1 | 9/2006 | Yang |
| 2006/0265739 | A1 | 11/2006 | Bhaskaran et al. |
| 2007/0005397 | A1 | 1/2007 | Lee |
| 2007/0021981 | A1 | 1/2007 | Cox |
| 2007/0168223 | A1 | 7/2007 | Fors et al. |
| 2007/0240231 | A1 | 10/2007 | Haswarey et al. |
| 2007/0244896 | A1 | 10/2007 | Liu et al. |
| 2007/0282843 | A1 | 12/2007 | Beck |
| 2008/0046987 | A1 | 2/2008 | Spector |
| 2008/0183547 | A1 | 7/2008 | Halaby |
| 2009/0019516 | A1 | 1/2009 | Hammoutene et al. |
| 2011/0029488 | A1 | 2/2011 | Fuerst et al. |

OTHER PUBLICATIONS

Final Office Action received for U.S. Appl. No. 12/981,032, dated May 31, 2018, 22 pages.
Non-Final Office Action received for U.S. Appl. No. 11/765,221, dated Mar. 29, 2010, 20 pages.
Non-Final Office Action received for U.S. Appl. No. 11/765,233, dated Apr. 13, 2010, 12 pages.
Non-Final Office Action received for U.S. Appl. No. 12/981,032, dated Sep. 20, 2017, 19 pages.
White et al., "How Computers Work", Oct. 15, 2003, Que Publishing, 43 pages.
David F. Ferraiolo, Role-Based Access Control (RBAC): Features and Motivations, 1995.
Ravi Sandhu, The NIST Model for Role-Based Access Control: Towards a Unified Standard, 2000.
Final Office Action received for U.S. Appl. No. 12/981,032, dated Jan. 15, 2020, 18 pages.
Non-Final Office Action received for U.S. Appl. No. 12/981,032, dated Mar. 22, 2019, 24 pages.

\* cited by examiner

```
┌─────────────────────────────────────────────────────────────────────────┐
│ ☐ SECURITY WIZARD                                                    X  │
├─────────────────────────────────────────────────────────────────────────┤
│ DEFINE POSITION SECURITY: SCHEDULING, LOCATION, ALLERGIES, PROBLEMS     │
│ AND DIAGNOSIS, AND PROCEDURES                                           │
├─────────────────────────────────────────────────────────────────────────┤
│ PCO SECURITY TASK PAGE: 1 OF 7   POSITION: PHYSICIAN ASSISTANT          │
│                                                                         │
│ SHOW PROCESSES BEING AUTOMATED AT THIS OFFICE OR CLINIC                 │
│ SELECT THE ACTIVITIES THAT THIS POSITION WILL BE AUTHORIZED TO PERFORM. │
│  ☑ VIEW A RESOURCE'S SCHEDULE (SCHEDULE)                                │
│  ☑ INDICATE THE PATIENT'S ARRIVAL/LOCATION IN THE CLINIC/OFFICE (LOCATOR)│
│  ┌─ ALLERGIES ─────────────────────────────────────────┐                │
│  │ ● ENTER/UPDATE A PATIENT'S ALLERGIES (ALLERGY PROFILE) │             │
│  │ ○ ONLY VIEW A PATIENT'S ALLERGIES (ALLERGY PROFILE)    │             │
│  │ ○ NO ACCESS TO A PATIENT'S ALLERGIES (ALLERGY PROFILE) │             │
│  └─────────────────────────────────────────────────────┘                │
│  ┌─ PROBLEMS AND DIAGNOSES ────────────────────────────┐                │
│  │ ● ENTER/UPDATE A PATIENT'S PROBLEMS & DIAGNOSES ...  │                │
│  │ ○ ONLY VIEW A PATIENT'S PROBLEMS & DIAGNOSES ...     │                │
│  │ ○ NO ACCESS TO A PATIENT'S PROBLEMS & DIAGNOSES ...  │                │
│  └─────────────────────────────────────────────────────┘                │
│  ┌─ PROCEDURES ────────────────────────────────────────┐                │
│  │ ● ENTER OR UPDATE A PATIENT'S PROCEDURE HISTORY ...  │                │
│  │ ○ ONLY VIEW A PATIENT'S ALLERGIES (ALLERGY PROFILE)  │                │
│  │ ○ NO ACCESS TO A PATIENT'S PROCEDURE HISTORY ...     │                │
│  └─────────────────────────────────────────────────────┘                │
│                                                                         │
│                                        [<BACK] [NEXT>] [FINISH] [CANCEL]│
└─────────────────────────────────────────────────────────────────────────┘
```

1100 — (screen)
1102 — (button row)

Side panel:
- USING THIS WIZARD
  - WHAT DATA WILL I NEED?
  - HOW LONG WILL THIS STEP TAKE?
  - WHY ARE SOME TASK OPTIONS UNAVAILABLE?
- MORE ABOUT THIS INFORMATION SYSTEM
  - LEARN MORE ABOUT THIS INFORMATION SYSTEM
  - GLOSSARY

SECURITY WIZARD

DEFINE POSITION SECURITY: FORMS, PEDIATRIC GROWTH CHART, PATIENT HISTORY, AND FLOWSHEET

1500

PCOSECURITY TASK PAGE: 5 OF 7    POSITION: PHYSICIAN ASSISTANT

SHOW PROCESSES BEING AUTOMATED AT THIS OFFICE OR CLINIC

SELECT THE ACTIVITIES THAT THIS POSITION WILL BE AUTHORIZED TO PERFORM.

FORMS
- ◉ CHART PATIENT INFORMATION IN A FORM (AD HOC CHARTING & FORM BROWSER)
- ○ VIEW AND ENTER PATIENT INFORMATION IN FORMS, BUT THE INFORMATION MUST BE VALIDATED BY SOMEONE ELSE (SUCH AS AN INSTRUCTOR OR PRECEPTOR) BEFORE IT IS CONSIDERED COMPLETE. EXAMPLE: NURSING STUDENTS (AD HOC CHARTING & FORM BORWSER)
- ○ ONLY VIEW PATIENT INFORMATION THAT WAS DOCUMENTED IN A FORM (FORM BROWSER)
- ○ NO ACCESS TO VIEW PATIENT INFORMATION THAT WAS DOCUMENTED IN A FORM (AD HOC CHARTING & FORM BROWSER)

☑ ENTER PATIENT INFORMATION INTO THE PEDIATRIC GROWTH CHART (PEDIATRIC GROWTH CHART)

PATIENT HISTORY
- ◉ ENTER/UPDATE A PATIENT'S HISTORY (PATIENT HISTORY PROFILE)
- ○ ONLY VIEW A PATIENT'S HISTORY (PATIENT HISTORY PROFILE)
- ○ NO ACCESS TO VIEW A PATIENT'S HISTORY (PATIENT HISTORY PROFILE)

☑ VIEW A PATIENT'S RESULTS (FLOWSHEETS)
  ☑ ADD A COMMENT TO A PATIENT'S RESULTS*
    - ◉ ADD COMMENTS TO ANY RESULT THAT HAS COME FROM A CERNER SOLUTION
    - ○ ADD COMMENTS TO ANY RESULT THAT THE USER PERFORMED THAT HAS COME FROM A CERNER SOLUTION
    - ○ ADD COMMENTS TO ANY RESULT THAT HAS COME EITHER FROM A CERNER SOLUTION OR A FOREIGN SYSTEM THROUGH AN INTERFACE

USING THIS WIZARD
- WHAT DATA WILL I NEED?
- HOW LONG WILL THIS STEP TAKE?
- WHY ARE SOME TASK OPTIONS UNAVAILABLE?

MORE ABOUT THIS INFORMATION SYSTEM
- LEARN MORE ABOUT THIS INFORMATION SYSTEM
- GLOSSARY

[< BACK] [NEXT >] [FINISH] [CANCEL]  1502

DEFINING PRIVILEGES IN ASSOCIATION WITH THE AUTOMATED CONFIGURATION, IMPLEMENTATION AND/OR MAINTENANCE OF A HEALTHCARE INFORMATION SYSTEM

CROSS-REFERENCE TO RELATED APPLICATIONS

This application is a continuation of copending U.S. application Ser. No. 11/765,221, entitled "Defining Privileges in Association with the Automated Configuration, Implementation and/or Maintenance of a Healthcare Information System, filed Jun. 19, 2007; which claims the benefit of U.S. Provisional Patent Application No. 60/805,169, filed Jun. 19, 2006, entitled "Automated Design, Build and/or Maintenance of a Healthcare Information System." This application is related by subject matter to U.S. patent application Ser. No. 11/765,233, entitled "Defining Privileges in Association with the Automated Configuration, Implementation and/or Maintenance of a Healthcare Information System," filed concurrently with application Ser. No. 11/765,221. Each of these applications is hereby incorporated by reference in its entirety.

BACKGROUND

Healthcare information systems are traditionally very institutionally customized and require a tremendous amount of time and effort to implement from ground level or convert from a different system. This is primarily because such systems are manually built which is a tedious process at best, generally taking several months and multiple in-person consultant visits to accomplish.

In particular, security and/or privileges are generally associated on an individualized basis. That is, for each individual having some access to the healthcare information system, security/privileges must be defined. Such process is rather time consuming when viewed in the context of the vast number of personnel that may have some access to the healthcare information system for varying reasons, e.g., data entry, auditing, order access, and the like.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments of the present invention relate to computerized systems, methods, and computer-readable media having computer-executable instructions embodied thereon, for configuring, implementing, and/or maintaining a customized healthcare information system. In embodiments, such configuring, implementing, and/or maintaining may include automated design and build of a customized healthcare information system from the ground level or may be an automated converting or updating process of a user's existing healthcare information system. The systems and methods of embodiments of the present invention utilize a number of information sources prior to configuration/implementation/maintenance to tailor or flex the process in a manner that is facility and/or personnel specific, thus alleviating solicitation of unnecessary information. Such information sources may include, by way of example only, one or more of facility- and personnel-specific content, facility and personnel profiles, help and knowledge assistance information, and pre-configured content. The more information to which the system has access for initiation and run of the configuration/implementation/maintenance process, the more tailored the process may be and, accordingly, the less time and effort will be required.

In embodiments, systems and methods of the present invention facilitate configuration, implementation, and/or maintenance of a healthcare information system through a series of screen displays designed to solicit pertinent information from a user wherein each subsequent screen display is selected based, at least in part, upon information extracted from one or more previously presented screen displays. In one embodiment, presentation of such screen displays is Web-based.

Accordingly, in one embodiment, the present invention relates to one or more computer-readable media having computer-executable instructions embodied thereof that, when executed, aid in defining privileges and/or security based on position upon configuring, implementing and/or maintaining a customized healthcare information system. The method includes receiving input of a position associated with a facility, the position having at least one configurable privilege associated therewith, presenting the configurable privilege (e.g., displaying the configurable privilege to a user defining the privileges associated with the position), receiving a configuration definition for the configurable privilege and storing the configuration definition in association with the privilege.

In an additional embodiment, the present invention relates to a user interface configured for defining privileges based on position in configuring, implementing and/or maintaining a customized healthcare information system. The user interface includes a selected positions display portion and an instructional display portion. The selected positions display portion is configured to display a list of positions associated with a facility, each position in the list having at least one configurable privilege associated therewith. The instructional display portion is configured to display instructions regarding one or more tasks to be completed in order to define the configurable privilege associated with at least one of the positions displayed in the list.

In a further embodiment, the present invention relates to a method for defining privileges based on position upon configuring, implementing and/or maintaining a customized healthcare information system. The method includes receiving input of a position associated with a facility, the position having at least one configurable privilege associated therewith, receiving a configuration definition for the configurable privilege(s), and storing the configuration definition in association with the configurable privilege(s).

In an additional embodiment, the present invention relates to one or more computer-readable media having computer-executable instructions embodied thereon that, when executed, aid in defining privileges based on position in configuring, implementing and/or maintaining a customized healthcare information system. The method includes receiving input of a position associated with a facility, the position having at least one configurable privilege associated therewith, receiving a configuration definition for the configurable privilege, determining if the configuration definition is consistent with at least one other configuration definition associated with the position, and storing the configuration definition in association with the configurable privilege.

Still further, embodiments of the present invention relate to a user interface configured for defining privileges based on position in configuring, implementing and/or maintaining a customized healthcare information system. The user interface includes a selected positions display portion, an instruction display portion and a reconciliation alert display portion. The selected positions display portion is configured to display a list of positions associated with a facility, each position in the list having at least one configurable privilege associated therewith. The instructional display portion is configured to display instructions regarding one or more tasks to be completed to define the at least one configurable privilege associated with at least one of the positions displayed in the list. The reconciliation alert display portion is configured to display a reconciliation alert if it is determined that a configuration definition associated with a given position is inconsistent with at least one other configuration definition associated with the given position.

In a further embodiment, the present invention relates to a method for defining privileges based on position in configuring, implementing and/or maintaining a customized healthcare information system. The method includes receiving input of a position associated with a facility, the position having at least one configurable privilege associated therewith, receiving a configuration definition for the at least one configurable privilege, determining if the configuration definition is consistent with at least one other configuration definition associated with the position and storing the configuration definition in association with the at least one configurable privilege.

BRIEF DESCRIPTION OF THE DRAWINGS

Embodiments of the present invention are described in detail below with reference to the attached drawing figures, wherein:

FIG. 11 is a screen display, in accordance with an embodiment of the present invention, of an exemplary user interface configured to permit a user to define position security with respect to scheduling, location, allergies, problems and diagnosis, and procedures;

FIG. 15 is a screen display, in accordance with an embodiment of the present invention, of an exemplary user interface configured to permit a user to define position security with respect to forms, pediatric growth chart, patient history, and flow sheets;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention relate to computerized systems, methods and computer-readable media having computer-executable instructions embodied thereon, for configuring, implementing, and/or maintaining a customized healthcare information system. In embodiments, such configuring, implementing, and/or maintaining may include automated design and build of a customized healthcare information system from the ground level or may be an automated converting or updating process of a user's existing healthcare information system. The systems and methods of embodiments of the present invention utilize input from a number of information sources prior to initiation of configuration/implementation/maintenance to tailor or flex the process in a manner that is facility and/or personnel specific, thus alleviating solicitation of unnecessary information. Such information sources may include, by way of example only, one or more of facility- and personnel-specific content, facility and personnel profiles, help and knowledge assistance information, and pre-configured content. The more information to which the system has access for initiation and run of the configuration/implementation/maintenance process, the more tailored the process may be and, accordingly, the less time and effort will be required.

Figure 1:
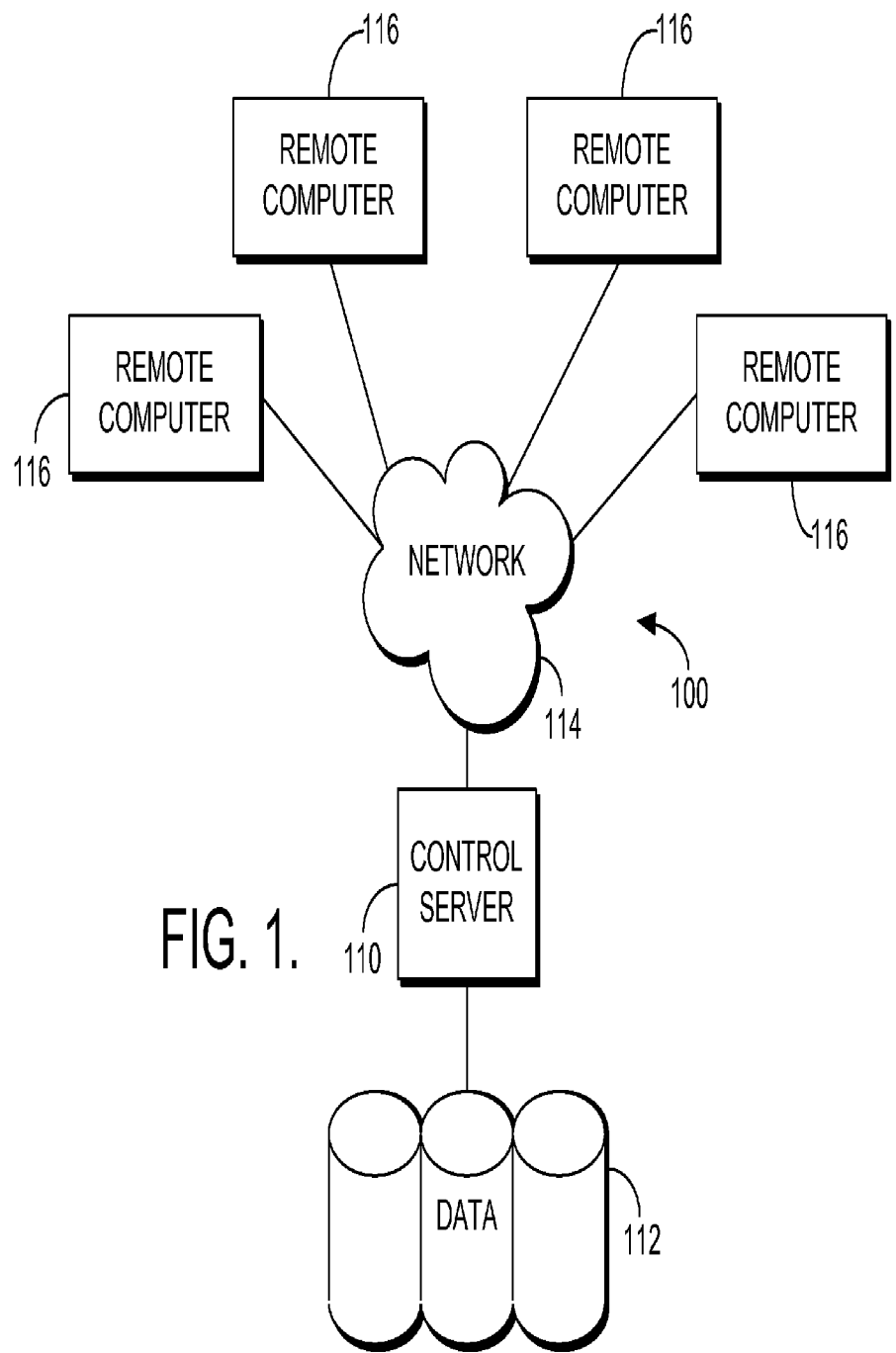
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component/module or combination of components/modules illustrated therein.

Embodiments of the present invention may be operational with numerous other general purpose or special purpose computing system environments or configurations. Examples of well-known computing systems, environments, and/or configurations that may be suitable for use with embodiments of the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 110. Components of the server 110 may include, without limitation, a processing unit, internal system memory, and a suitable system bus for coupling various system components, including database cluster 112, with the server 110. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 110 typically includes, or has access to, a variety of computer-readable media, for instance, database cluster 112. Computer-readable media can be any available media that may be accessed by server 110, and includes volatile and nonvolatile media, as well as removable and non-removable media. By way of example, and not limitation, computer-readable media may include computer storage media and communication media. Computer storage media may include, without limitation, volatile and non-volatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 110. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 112, provide storage of computer-readable instructions, data structures, program modules, and other data for the server 110.

The server 110 may operate in a computer network 114 using logical connections to one or more remote computers 116. Remote computers 116 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. The remote computers 116 may also be physically located in non-traditional medical care environments so that the entire health care community may be capable of integration on the network 114. The remote computers 116 may be personal computers, servers, routers, network PCs, peer devices, other common network nodes, or the like, and may include some or all of the elements described above in relation to the server 110. The devices can be personal digital assistants or other like devices.

Exemplary computer networks 114 may include, without limitation, local area networks (LANs) and/or wide area networks (WANs). Such networking environments are commonplace in offices, enterprise-wide computer networks, intranets, and the Internet. When utilized in a WAN networking environment, the server 110 may include a modem or other means for establishing communications over the WAN, such as the Internet. In a networked environment, program modules or portions thereof may be stored in the server 110, in the database cluster 112, or on any of the remote computers 116. For example, and not by way of limitation, various application programs may reside on the memory associated with any one or more of the remote computers 116. It will be appreciated by those of ordinary skill in the art that the network connections shown are exemplary and other means of establishing a communications link between the computers (e.g., server 110 and remote computers 116) may be utilized.

In operation, a user may enter commands and information into the server 110 or convey the commands and information to the server 110 via one or more of the remote computers 116 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 110. In addition to a monitor, the server 110 and/or remote computers 116 may include other peripheral output devices, such as speakers and a printer.

Although many other internal components of the server 110 and the remote computers 116 are not shown, those of ordinary skill in the art will appreciate that such components and their interconnection are well known. Accordingly, additional details concerning the internal construction of the server 110 and the remote computers 116 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the automated configuration, implementation and/or maintenance of a healthcare information system. As contemplated by the language above, the methods and systems of embodiments of the present invention may also be implemented on a stand-alone desktop, personal computer, or any other computing device used in a healthcare environment or any of a number of other locations.

Figure 2:
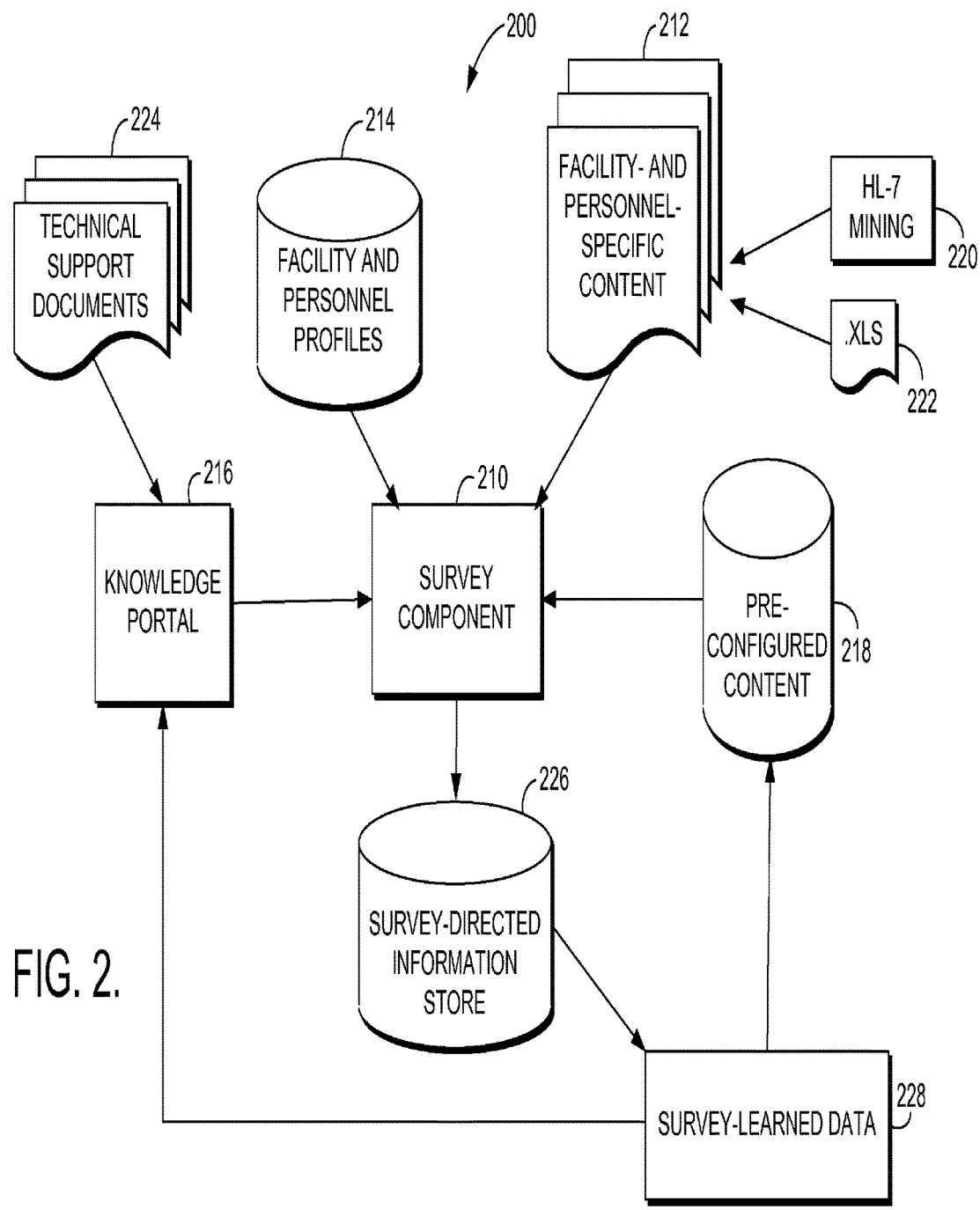
FIG. 2 is a block diagram of an exemplary system architecture for use in implementing embodiments of the present invention.

As previously mentioned, the present invention relates to computerized systems and methods for the automated configuration, implementation and/or maintenance of a healthcare information system. Turning to FIG. 2, an exemplary system architecture for use in implementing embodiments of the present invention is illustrated and designated generally as reference numeral 200. It will be understood and appreciated by those of ordinary skill in the art that the overall system architecture 200 shown in FIG. 2 is merely an example of one suitable system architecture and is not intended to suggest any limitation as to the use or functionality of the present invention. Neither should the overall system architecture 200 be interpreted as having any dependency or requirement related to any single component/module or combination of components/modules illustrated therein.

System 200 includes a survey component 210 configured to receive input from a number of content components. Such content components include a facility- and personnel-specific content component 212, a facility and personnel profile content component 214, a knowledge portal 216 and a pre-configured content component 218. It will be understood and appreciated by those of ordinary skill in the art that the number and nature of the inputs into the survey component 210 are merely exemplary and are not intended to limit the scope of embodiments of the present invention in any way.

The facility- and personnel-specific content component 212 includes localized data derived from the particular facility, group of facilities, facility network, facility portion, or the like that desires to configure, implement and/or maintain the customized healthcare information system. Such localized data may include, by way of example only, clinician and other personnel lists, the physical address of one or more healthcare locations operated by the user, the facility organization and design of one or more healthcare locations operated by the user, patient profiles, user preferences, user-specific orderable items and any associated aliases and/or collection requirements, work routing preferences, and the like. Basically, the localized data includes any data that is unique to the particular facility, facility portion, facility group, etc. that desires to configure, implement and/or maintain the healthcare information system in question and that cannot be estimated or derived absent specific input or interaction with such data. Such data may be input into the facility- and personnel-specific content component 212 from a variety of sources including, by way of example only, data collected through Health Level 7 (HL-7) mining 220 of the facility's existing healthcare information system and/or data collected through facility- or personnel-specific tables or spreadsheets 222, which may be manually or automatically populated. Facility- and personnel-specific content component 212 is generally utilized in situations where the facility (facility portion, facility group, or the like) has an existing healthcare information system and desires to have such system updated or modified or to have a different healthcare information system configured and/or implemented. If necessary, upon extraction of data from the facility- and personnel-specific content component 212, such data is formatted to the requirements of the survey component 210 and input therein.

Facility and personnel profile component 214 includes high-level data about the nature of the facility (facility portion, facility group, etc.) and/or associated personnel. For instance, the facility and personnel profile component 214 may include data regarding what particular solutions the facility (facility portion, facility group, etc.) desires to have configured, implemented and/or maintained in its healthcare information system or data regarding what type of healthcare facility (facilities, facility portions, etc.) being operated (e.g., a children's hospital, an academic hospital, or the like). Such information is typically collected during cursory conversations or meetings, or preliminary fact-finding scenarios with respect to a particular facility (or the like) and input into the facility and personnel profile component 214. If necessary, upon extraction of data from the facility and personnel profile component 214, such data is formatted to the requirements of the survey component 210 and input therein.

Knowledge portal 216 is configured to access and/or provide informational assistance data that will be available during configuration, implementation and/or maintenance of the healthcare information system, such data generally being presented in a natural language format. For instance, the knowledge portal 216 may include, by way of example only and not limitation, instruction on how to use the survey component 210, instruction on how to use a particular screen display presented during use of the survey component 210, information regarding the reasoning for attempting to extract a particular piece of data from a user, data supporting the ramifications of selecting one option over another (including real-life examples), definitions of terms, frequently asked questions, graphical displays, work charts, representations of front-end applications, and the like. Such information may be input into the knowledge portal 216 from a variety of sources including, by way of example only and not limitation, extraction from technical support documents 224. In this regard, data may not simply be transferred from the technical support documents 224 into the knowledge portal 216 but may be converted from technical language to a more natural, user-friendly language upon input into the knowledge portal 216.

The knowledge portal 216 may additionally include data input from survey-learned data component 228, which component is more fully discussed herein below. If necessary, upon extraction of data from the knowledge portal 216, such data is formatted to the requirements of the survey component 210 and input therein.

Pre-configured content component 218 includes content that is pre-configured to be relevant in configuring, implementing and/or maintaining the desired for building the healthcare information system in question. In this regard, the pre-configured content may be based, at least in part, upon the preferences and/or regulations of a particular healthcare system, the preferences and/or regulations of healthcare systems in a particular country or region, or the like. The pre-configured content includes survey-specific tables that contain all of the options a user/facility may desire with respect to healthcare information system configuration, implementation and/or maintenance. The pre-configured content further includes information regarding typical healthcare information system configurations for, e.g., particular types of healthcare facilities, and the like. In this regard, if a facility (facility group, facility portion, or the like) does not have an existing healthcare information system and, accordingly, such system is being configured and/or implemented from the ground level, such configuration/implementation may be seeded with data derived from such pre-configured, typical configurations as opposed to seeded with facility- and personnel-specific data input from the facility- and personnel-specific content component 212 as would be the case if the user had an existing healthcare information system. In one embodiment, content from each of the pre-configured content component 218 and the facility- and personnel-specific content component 212 is input into the survey component 210 for utilization in configuring, implementing and/or maintaining a healthcare information system. Any and all such variations and combinations thereof are contemplated to be within the scope of embodiments of the present invention.

Data concerning typical healthcare information system configurations and preferences may be derived, at least in part, from survey-learned information stored in association with survey-learned data component 228. Survey-learned data component 228 includes data that has been mined or extracted from the survey-directed information store 226, which information store contains data associated with each configuration, implementation and/or maintenance of the healthcare information system. Thus, with respect to the healthcare information system being configured/implemented/maintained, the survey-directed information store 226 includes clinical or common best practices, facilities data, and the like. The survey-directed information store is more fully discussed herein below.

Survey component 210 is configured not only to receive various inputs as described above, but also to present a plurality of screen displays from which a user may input information to customize the healthcare information system being configured, implemented and/or maintained. Such screen displays may be presented on any type of computing device, for instance, a user's personal computer, desktop computer, laptop computer, handheld device, consumer electronic device, and the like. It should be noted, however, that the invention is not limited to implementation on such computing devices, but may be implemented on any of a variety of different types of computing devices within the scope of embodiments of the present invention. Typically, presentation of the screen displays comprises displaying the screen displays on a display device associated with a computing device as discussed above. However, other types of presentation, such as audible presentation, may also be provided within the scope of embodiments of the present invention.

The screen displays which are presented by the survey component 210 are selected based upon at least a portion of the information input into the survey component 210. Thus, the screen displays that are presented by the survey component 210 are flexed based upon the information already available to the survey component 210 prior to user interaction with the screen displays. Accordingly, the screen displays that are available for user input and interaction will vary for each facility (facility group, facility portion, etc.) configuring, implementing and/or maintaining the healthcare information system in question. Additionally, as the user interacts with each of the screen displays presented and inputs additional information into the system, each subsequent screen display is selected for presentation taking into account that information. In this way, the healthcare information system configuration, implementation and/or maintenance process is customized for each facility (facility group, facility portion, and the like), significantly decreasing the time and effort such configuration/implementation/maintenance may take. Customization of the healthcare information system and exemplary user-directed screen displays are discussed more fully herein below with reference to FIGS. 4-30.

The survey component 210 is further configured to output facility- and personnel-specific data to a survey-directed information store 226 once information has been input, and presented to and customized by a user. Only that information which was selected by and/or customized by the user is output to the information store 226 and, as such, the information in the information store 226 is both facility- and personnel-specific and survey-directed. The information in the survey-directed information store 226 is subsequently available for mining and extraction by the survey-learned data component 228 and, if desired, input into the pre-configured content component 218 and/or knowledge portal 216. In this way, the healthcare information system 200 gets "smarter" with each configuration/implementation/maintenance run, that is, it has additional information available to it that allows it to further customize and direct the user through the process.

Figure 3:
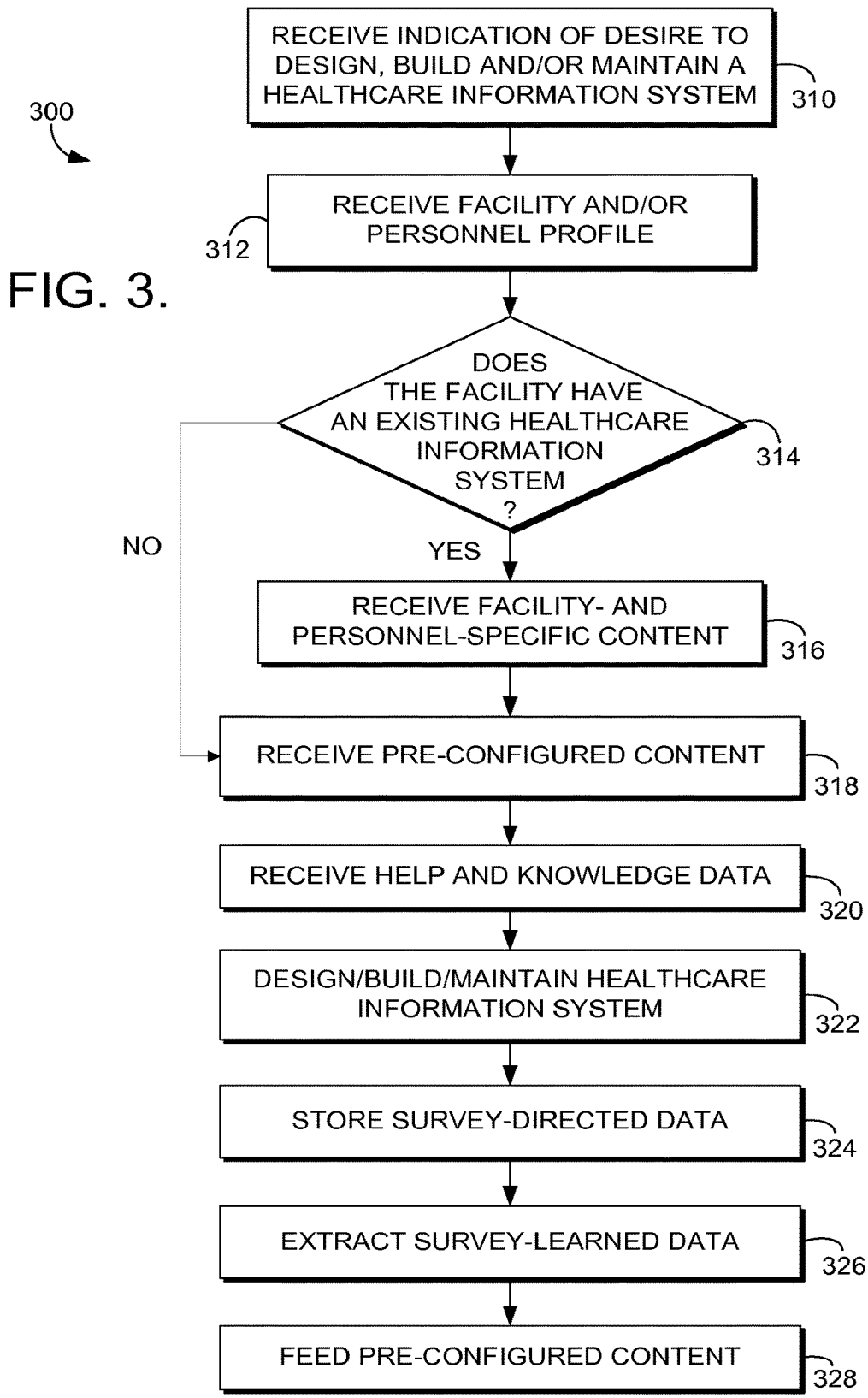
FIG. 3 is a flow diagram, in accordance with an embodiment of the present invention, illustrating a method for configuring, implementing and/or maintaining a healthcare information system.

Turning to FIG. 3, a flow diagram is illustrated which shows an exemplary method 300 for automated configuration, implementation and/or maintenance of a healthcare information system, in accordance with an embodiment of the present invention. Initially, as indicated at block 310, an indication that a user associated with a facility (group of facilities, facility portion, or the like) desires to configure, implement or maintain a healthcare information system is received. Such indication may be received, for instance, upon user selection of a "survey" icon present on the desktop of a display associated with the user's computing device. Subsequently, an accessible facility and/or personnel profile for the facility (group of facilities, facility portion, etc.) associated with the user is received, as indicated at block 312. Such facility and/or personnel profile may be received, for instance, by survey component 210 from facility and personnel profile component 214 of FIG. 2.

Next, it is determined whether or not the facility(ies) associated with the user has an existing healthcare information system. This is indicated at block 314. Such determination may be made, for instance, by survey component 210 of the system architecture 200 of FIG. 2. If it is determined that the facility(ies) associated with the user does have an existing healthcare information system, facility- and/or personnel-specific content derived from the existing healthcare information system is subsequently received, as indicated at block 316. Such facility- and personnel-specific content may be received, for instance, by survey component 210 from facility- and personnel-specific content component 212 of FIG. 2.

Subsequently, or if it is determined at block 314 that the facility (facilities, facility portion, or the like) associated with the user does not have an existing healthcare information system, pre-configured content that is pre-configured to be relevant in configuring, implementing and/or maintaining the healthcare information system is received. This is indicated at block 318. Such pre-configured content may be received, for instance, by survey component 210 from pre-configured content component 210 of FIG. 2. Subsequently, prior to, or simultaneously, help and knowledge data is received, as indicated at block 320. Such help and knowledge data may be received, by way of example only and not limitation, by survey component 210 of FIG. 2 from knowledge portal 216.

It will be understood and appreciated by those of ordinary skill in the art that the order of steps 310, 312, 314, 316, 318, and 320 is presented by way of example only and is not intended to limit the scope of the invention in any way. Input from each of the various sources of information may be received simultaneously, consecutively and/or in any order. Additionally, information from any one or more of the various information sources may be received within embodiments hereof. All such variations are contemplated to be within the scope of embodiments of the present invention.

Once all available information has been received, the healthcare information system is configured, implemented, updated, and/or maintained as indicated at block 322. Such configuration/implementation/maintenance may be conducted, for instance, utilizing a series of screen displays presented to the user as described hereinabove. (One exemplary series of screen displays for implementing general lab order catalog functionality is more fully described below with reference to FIGS. 4-30.) Once the configuration, implementation and/or maintenance run is complete, the facility- and personnel-specific, survey-directed information is stored, as indicated at block 324. Such information may be stored, for instance, in the facility- and personnel-specific, survey-directed information store 226 (or database) of the system architecture 200 of FIG. 2.

If desired, the survey-learned data may be mined, extracted, or otherwise retrieved for utilization in future implementations, updates and/or maintenance of the healthcare information system. This is indicated at block 326. In one embodiment, the survey-learned data may be extracted by survey-learned data component 228 from the facility- and personnel-specific, survey-directed information store 226 of FIG. 2 utilizing data mining techniques known to those of ordinary skill in the art. Subsequently, as indicated at block 328, the survey-learned data may be fed, for instance, in the pre-configured content component 218 and/or the knowledge portal component 216 of FIG. 2. In this way, the system improves, or becomes "smarter," with each consecutive run.

Turning now to FIGS. 4-7, a series of exemplary screen displays for selecting processes to be automated in association with a healthcare information system being configured, implemented and/or maintained is provided. It will be understood and appreciated by those of ordinary skill in the art that the series of screen displays presented in FIGS. 4-7 is exemplary in nature and is not intended to limit the scope of the invention in any way. Though not shown, it will additionally be understood and appreciated by those of ordinary skill in the art that the automated process selection process may be initiated upon user selection of an indicator representing such processes from a list of available processes and/or processes that are to be completed prior to operation of the healthcare information system being configured, implemented and/or maintained.

Figure 4:
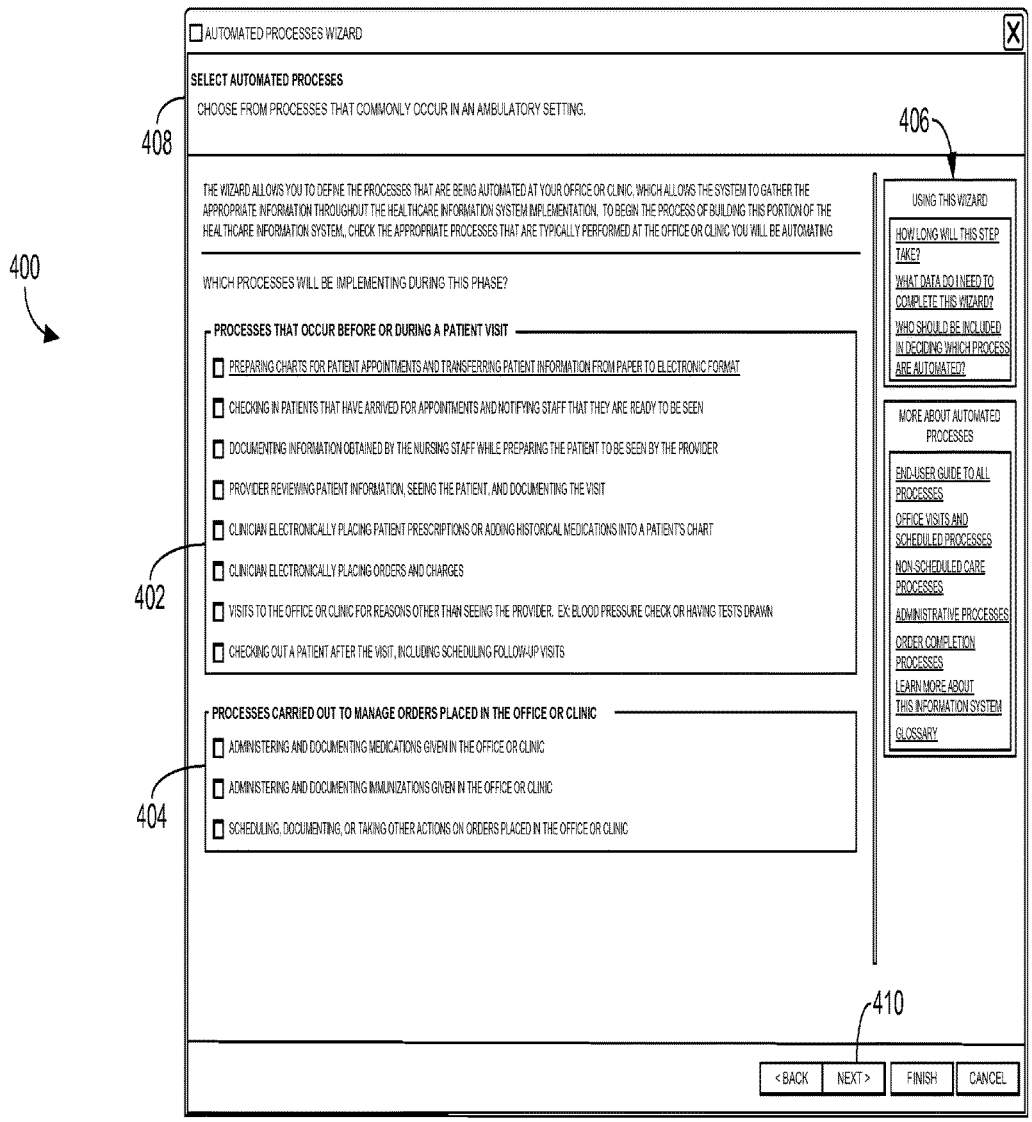
FIG. 4 is a screen display of an exemplary user interface that may be displayed upon user initiation of a process configured to permit selection of processes that commonly occur in an ambulatory setting that the user desires to automate, such processes typically occurring before or during a patient visit and/or configured to manage orders placed in the office or clinic, in accordance with an embodiment of the present invention.
Figure 5:
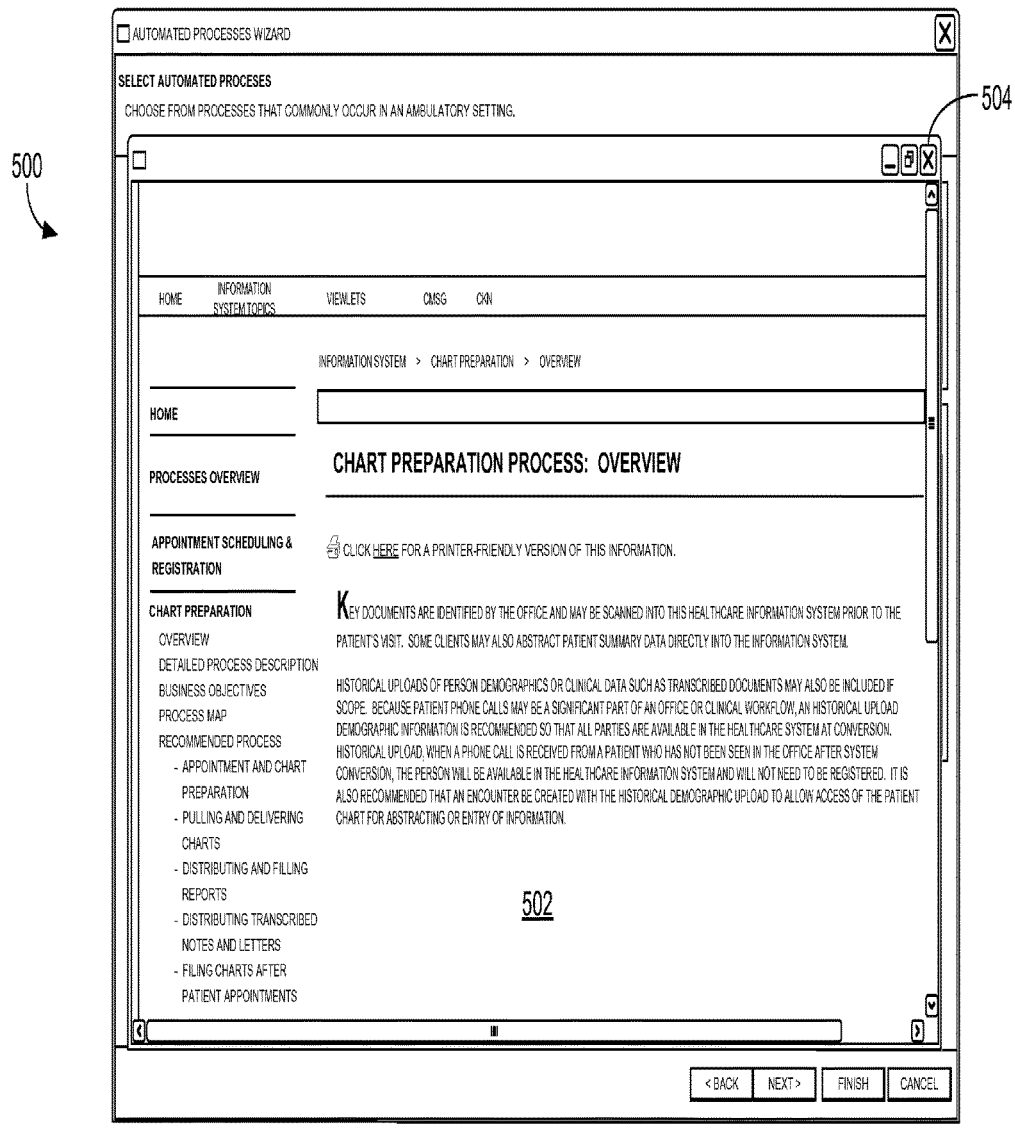
FIG. 5 is a screen display, in accordance with an embodiment of the present invention, of an exemplary user interface that may be displayed upon selection of the "Preparing charts for patient appointments and transferring patient information from paper to electronic format" hyperlink of FIG. 4.

With initial reference to FIG. 4, an exemplary user interface illustrating a number of user-directed wizards that may be run in order to configure and/or modify particular functionalities upon configuration, implementation and/or maintenance of a healthcare information system is illustrated and designated generally as reference numeral 400. Note that each of the designated processes is provided with a natural language descriptor to help users more readily understand what he is being asked to do. Such a more complete understanding may decrease the time it takes a user to complete the automated process selection method and, accordingly, increase user satisfaction.

User interface 400 includes a listing of available processes display portion 402, each of the listed processes typically occurring before or during a patient visit, a managed order display portion 404 including a list of available processes carried out to manage orders placed in the office or clinic, and a help and knowledge display portion 406. The available processes display portion 402 is configured to display selectable links for each process that typically occurs before or during a patient visit that is available to the user during configuration, implementation and/or maintenance. Similarly, the managed order display portion 404 is configured to display selectable links for each process that is typically carried out to manage orders placed in the office or clinic that is available to the user during configuration, implementation and/or maintenance. The processes shown in the available processes display portion 402 and the managed order display portion 404 are selected based upon the information input into, for instance, the survey component 210 of the system architecture 200 of FIG. 2. Additionally, the user may complete a site profile (not shown) prior to initiation of the healthcare information system configuration, implementation and/or maintenance and the information gleaned from such site profile may be input (e.g., into the facility and personnel profiles component 214) prior to initiation of the automated process selection method. As the system has access to this information prior to initiation of the healthcare information system functionalities described herein, the processes shown are only those which pertain to the user, relate to processes that are available in the healthcare information system the user is configuring, implementing and/or maintaining, and that pertain to the phase of configuration, implementation and/or maintenance being run by the user. As such, each of the display portions 402 and 404 of FIG. 4 will display customized lists of processes for each user initiating configuration, implementation and/or maintenance of a healthcare information system.

The name or designation for each of the processes listed in the available processes display portion 402 and the managed order display portion represents a selectable link to additional information pertaining to the named process, such information being derived, for instance, from the knowledge portal 216 of the system architecture 200 of FIG. 2. By way of example only and not limitation, with reference to FIG. 5, an exemplary user interface that may be displayed upon selection of the "Preparing charts for patient appointments and transferring patient information from paper to electronic format" process listed in the available processes display portion 402 of user interface 400 is illustrated and designated generally as reference numeral 500. User interface 500 includes an informational display portion 502 configured to display information to the user that pertains to the selected process, i.e., the chart preparation process. User interface 500 additionally includes a help and knowledge display portion 502 configured to display selectable links to data which may be helpful to the user in determining if he would like to automate the selected process. By way of example only, such data may include a process map, content to support the benefits and downsides of automating the selected process, and/or recommendations. Such data may be derived, for instance, from the knowledge portal 216 of the system architecture 200 of FIG. 2.

Once the user has completed review of the information displayed in the informational display portion 502, he may select the close indicator 504 to close the display of user interface 500 and return to the user interface 400 of FIG. 4.

Referring back to FIG. 4, the help and knowledge display portion 406 of user interface 400 is configured to display one or more selectable links to additional information that may be of use to the user in completing the healthcare information system configuration, implementation and/or maintenance. Such additional information may be derived, for instance, from knowledge portal 216 of the system architecture 200 of FIG. 2.

User interface 400 additionally includes an instructional display portion 408 and a selectable "Next" indicator 410. The instructional display portion 408 is configured to display instructions which inform the user what tasks he is to complete with respect to user interface 400. As indicated in the instructional display portion 408, the user is to "[c]hoose from processes that commonly occur in an ambulatory setting." That is, the user is instructed to select the indicator box next to each of the processes designated in display portions 402 and 404 that he desires to automate. Once the user has completed selection of the process(es) for which automation is desired, such processes typically occurring before or during a patient visit and/or typically carried out to manage orders placed in the office or clinic, he may select the selectable "Next" indicator 410. Selection of the "Next" indicator 410 may initiate display of the exemplary user interface 600 of FIG. 6.

User interface 600 illustrates a number of additional processes that may be automated upon configuration, implementation and/or maintenance of a healthcare information system. User interface 600 includes an available processes for patient care display portion 602 having a list of available process for patient care that occur outside the office visit; an information management display portion 604 including a list of management-type processes, for instance, health information management, billing, and administrative management; and a help and knowledge display portion 606. The available processes for patient care display portion 602 is configured to display selectable links for each process for patient care that typically occurs outside of the office visit that is available to the user for configuration, implementation and/or maintenance. Similarly, information management display portion 604 is configured to display selectable links for each processes that is typically included in health information management, billing, and administrative management that is available to the user for configuration, implementation and/or maintenance. The processes shown in processes for patient care display portion 602 and the information management display portion 604 are selected based upon the information input into, for instance, the survey component 210 of the system architecture 200 of FIG. 2 and/or information gleaned from a site profile (e.g., input into the facility and personnel profiles component 214). In this regard, the processes shown are only those which pertain to the user, relate to processes that are available in the healthcare information system the user is configuring, implementing and/or maintaining, and that pertain to the phase of configuration, implementation and/or maintenance being run by the user. As such, each of the display portions 602 and 604 of FIG. 6 will display customized lists of processes for each user initiating configuration, implementation and/or maintenance of a healthcare information system.

The name or designation for each of the processes listed in processes for patient care display portion 602 and the information management display portion 604 represents a selectable link to additional information pertaining to the named process, such information being derived, for instance, from knowledge portal 216 of the system architecture 200 of FIG. 2.

The help and knowledge display portion 606 of user interface 600 is configured to display one or more selectable links to additional information that may be of use to the user in completing the healthcare information system configuration, implementation and/or maintenance. Such additional information may be derived, for instance, from knowledge portal 216 of the system architecture 200 of FIG. 2.

User interface 600 additionally includes an instructional display portion 608, a selectable "Next" indicator 610, and a selectable "Finish" indicator 612. The instructional display portion 608 is configured to display instructions which inform the user what tasks he is to complete with respect to user interface 600. As indicated in the instructional display portion 608, the user in the illustrated embodiment is to "[c]hoose from processes that occur outside the office and other administrative processes." That is, the user is instructed to select the indicator box next to each of the processes designated in display portions 602 and 604 that he desires to automate.

Once the user has completed selection of the processes for which automation is desired from display portions 602 and 604, it is determined whether or not the user has selected any processes from user interfaces 400 (FIG. 4) and 600 (FIG. 6) that require documentation options to be selected. Such processes requiring selection of documentation options may include, by way of example only, "[d]ocumenting information obtained by the nursing staff while preparing the patient to be seen by the provider", "[p]rovider reviewing patient information, seeing the patient, and documenting the visit", "[c]linician electronically placing patient prescriptions or adding historical medications into the patient's chart", and "[c]linician electronically placing orders and charges", each process being listed in the available processes display portion 402 of FIG. 4.

Figure 6:
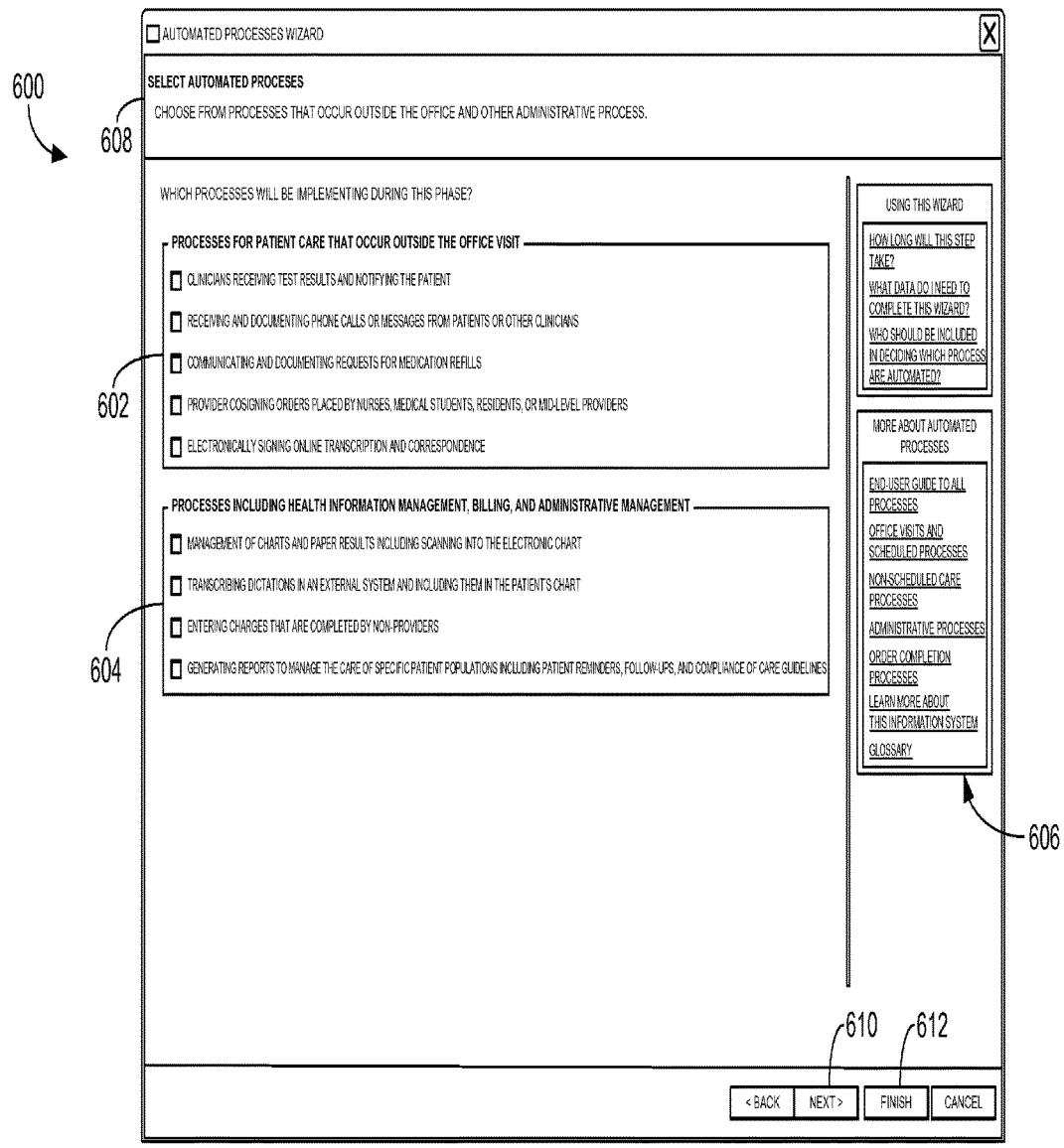
FIG. 6 is a screen display of an exemplary user interface that may be displayed to permit user selection of processes that commonly occur in an ambulatory setting that the user desires to automate, such processes typically occurring outside of an office visit and/or including health information management, billing, and administrative management, in accordance with an embodiment of the present invention.

If the user has selected one or more processes requiring selection of documentation options, the selectable "Next" indicator 610 of the user interface 600 of FIG. 6 will be available for selection by the user. If, however, the user has not selected one or more processes requiring selection of documentation options, the selectable "Next" indicator 610 will not be available for selection by the user. In such case, the user will typically select the selectable "Finish" indicator 612 to indicate completion of the selection of automated processes selection method.

Figure 7:
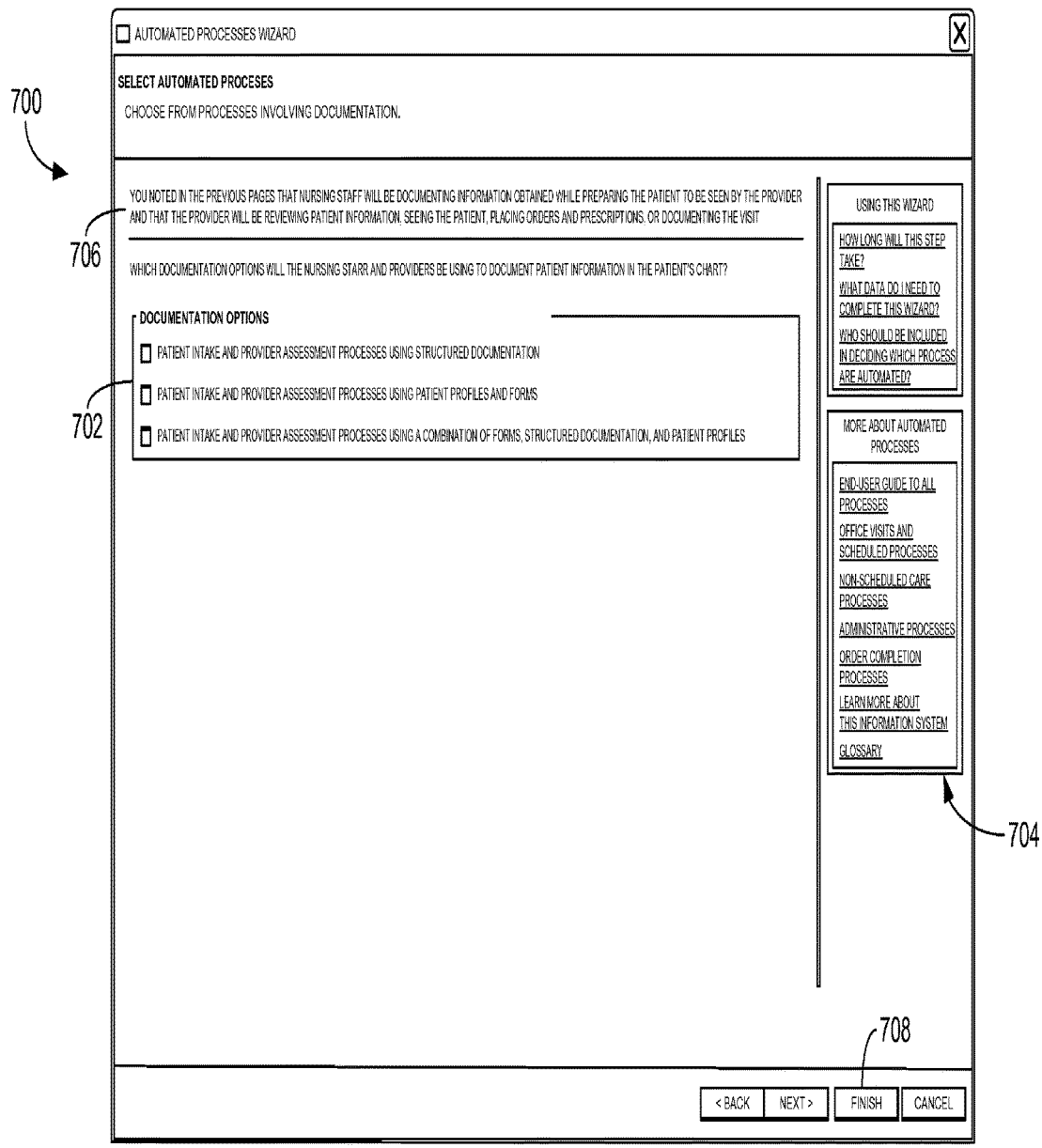
FIG. 7 is a screen display of an exemplary user interface that may be displayed to permit user selection of processes that commonly occur in an ambulatory setting that the user desires to automate, such processes pertaining to documentation, in accordance with an embodiment of the present invention.

If the "Next" indicator 610 is available for selection and selected by the user, the exemplary user interface 700 of FIG. 7 may be displayed. User interface 700 includes a documentation options display portion 702 and a help and knowledge display portion 704. The documentation options display portion 702 is configured to display selectable links for each documentation option that is available to the user for configuration, implementation and/or maintenance. The options shown in the documentation options display portion 702 are selected based upon the information input into, for instance, the survey component 210 of the system architecture 200 of FIG. 2 and the processes the user has selected for automation that require selection of documentation options. In this regard, the options shown are only those which pertain to the user, relate to options that are available in the healthcare information system the user is configuring, implementing and/or maintaining, and that pertain to the phase of configuration, implementation and/or maintenance being run by the user. As such, the display portion 702 of FIG. 7 will display a customized list of options for each user initiating configuration, implementation and/or maintenance of a healthcare information system.

The name or designation for each of the options listed in the documentation options display portion 702 represents a selectable link to additional information pertaining to the named option, such information being derived, for instance, from knowledge portal 216 of the system architecture 200 of FIG. 2.

The help and knowledge display portion 704 of user interface 700 is configured to display one or more selectable links to additional information that may be of use to the user in configuring, implementing and/or maintaining the healthcare information system. Such additional information may be derived, for instance, from knowledge portal 216 of the system architecture 200 of FIG. 2.

User interface 700 additionally includes an instructional display portion 706 and a selectable "Finish" indicator 708. The instructional display portion 706 is configured to display instructions which inform the user what tasks he is to complete with respect to user interface 700. As indicated in the instructional display portion 708 in the illustrated embodiment, the user has "noted in the previous pages that nursing staff will be documenting information obtained while preparing the patient to be seen by the provider and that the provider will be reviewing patient information, seeing the patient, placing orders and prescriptions, or documenting the visit." Accordingly, the user is asked "[w]hich documentation options will the nursing staff and providers be using to document patient information in the patient's chart?" That is, the user is instructed to select the indicator box next to one of the options designated in display portion 702 that describes the documentation option(s) the nursing staff and providers will be using. Once the user has completed selection of the desired documentation option(s), he may select the selectable "Finish" indicator 708 to indicate completion of the automated processes selection method.

Turning now to FIGS. 8-22, a series of exemplary screen displays representing a process for defining security for each of the positions in the clinical setting associated with a healthcare information system being configured, implemented and/or maintained is provided. It will be understood and appreciated by those of ordinary skill in the art that the series of screen displays presented in FIGS. 8-22 is exemplary in nature and is not intended to limit the scope of the invention in any way. Though not shown, it will additionally be understood and appreciated by those of ordinary skill in the art that the security/privileges process may be initiated upon user selection of an indicator representing such process from a list of available processes and/or processes that are to be completed prior to operation of the healthcare information system being configured, implemented and/or maintained.

The process represented in FIGS. 8-22 permits user to assign privileges at the position level such that all personnel designated to a particular position will have the same security rights, absent any specifically delineated exceptions. Assigning such privileges at the position level alleviates the need for a user to designate security rights for each individual having access to the healthcare information system being configured, implemented and/or maintained.

Figure 8:
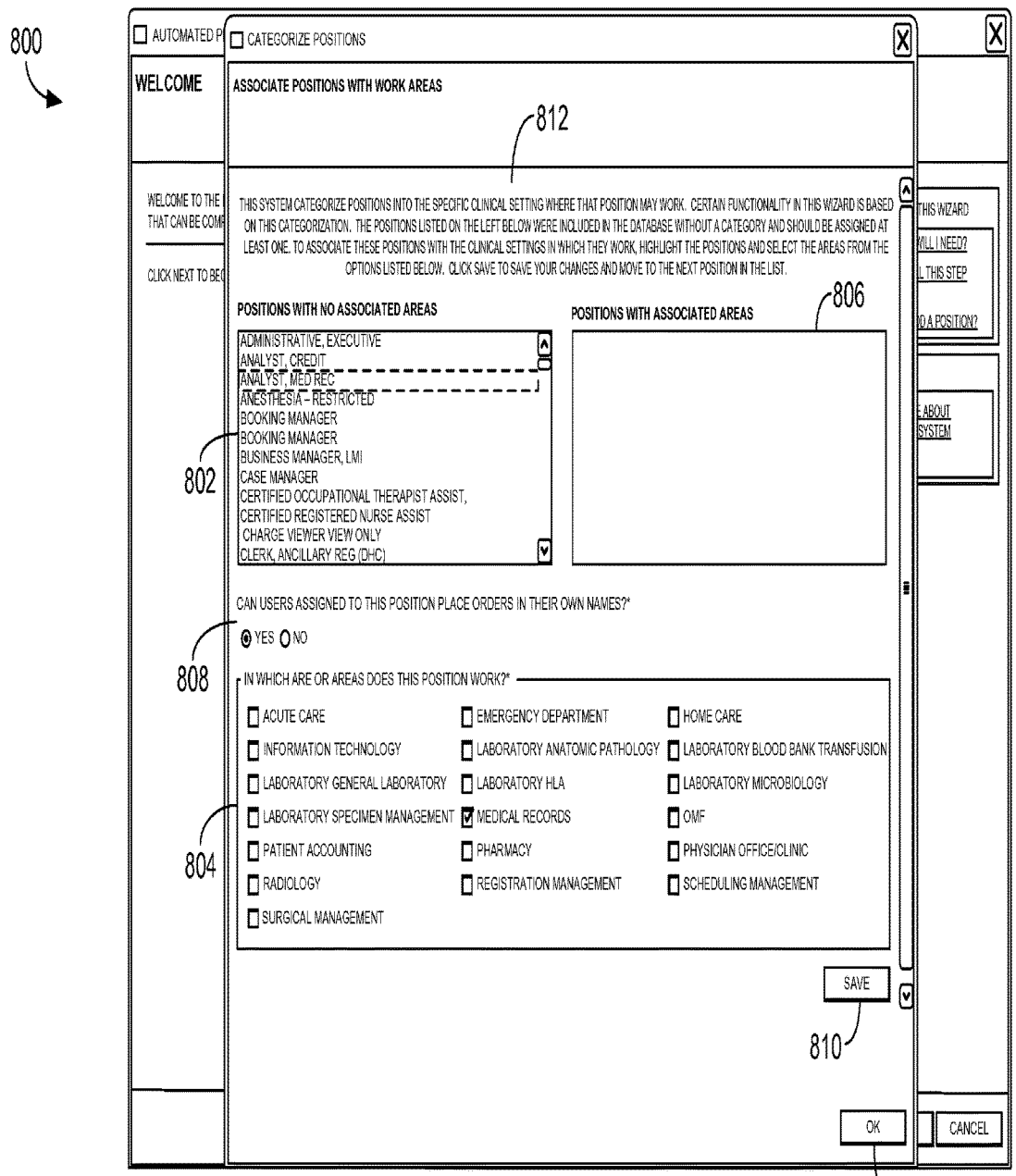
FIG. 8 is a screen display of an exemplary user interface configured to permit a user to associate positions that exist in a healthcare information system being utilized by the user that is other than the healthcare information system being configured, implemented and/or maintained with categories to be utilized for setting privileges available to personnel assigned to that position, in accordance with an embodiment of the present invention.

With initial reference to FIG. 8, an exemplary user interface configured to permit a user to associate positions that exist in a healthcare information system being utilized by the user that is other than the healthcare information system being configured, implemented and/or maintained with categories to be utilized for setting privileges available to personnel assigned to that position is shown and designated generally as reference numeral 800. User interface 800 includes a positions with no association display portion 802, a work area or category designation display portion 804, and a positions with associated areas display portion 806. The positions with no association display portion 802 is configured to display a list of those positions currently designated in the healthcare information system being utilized by the user that is other than the healthcare information system being configured, implemented and/or maintained. The displayed list of positions may be derived, for instance, from the facility and personnel profiles component 214 of the system architecture 200 of FIG. 2. The work area or category designation display portion 804 is configured to display a number of work areas or categories with which each of the unassociated positions may be associated. The positions with associated areas display portion 806 is configured to display those positions which have been associated with a particular work area or category once such designation is made by the user.

In practice, a user may select one of the positions listed in the positions with no associated areas positions with no association display portion 802 and subsequently select the check box next to one or more work area or category designations from the work area or category designation display portion 804. The user may also indicate whether personnel assigned to the position in question can place orders in their own names in an order security display area 808. Once all work areas or categories associated with the selected position have been designated, the user may select the "Save" indicator 810. Upon such selection, the position in question will be moved from positions with no association display portion 802 to the positions with associated areas display portion 806. The user may then repeat the process for each position that has no category designation that he desires to categorize for purposes of setting security/privileges.

User interface 800 additionally includes an instructional display portion 812 configured to display instructions which inform the user what tasks he is to complete with respect to user interface 800 and detailed instructions regarding how to accomplish those tasks. Once all positions displayed in the positions with no association display portion 802 that the user desires to categorize have been categorized, the user may select the selectable "OK" indicator 814 to begin setting security/privileges for all positions he desires to automate.

Figure 9:
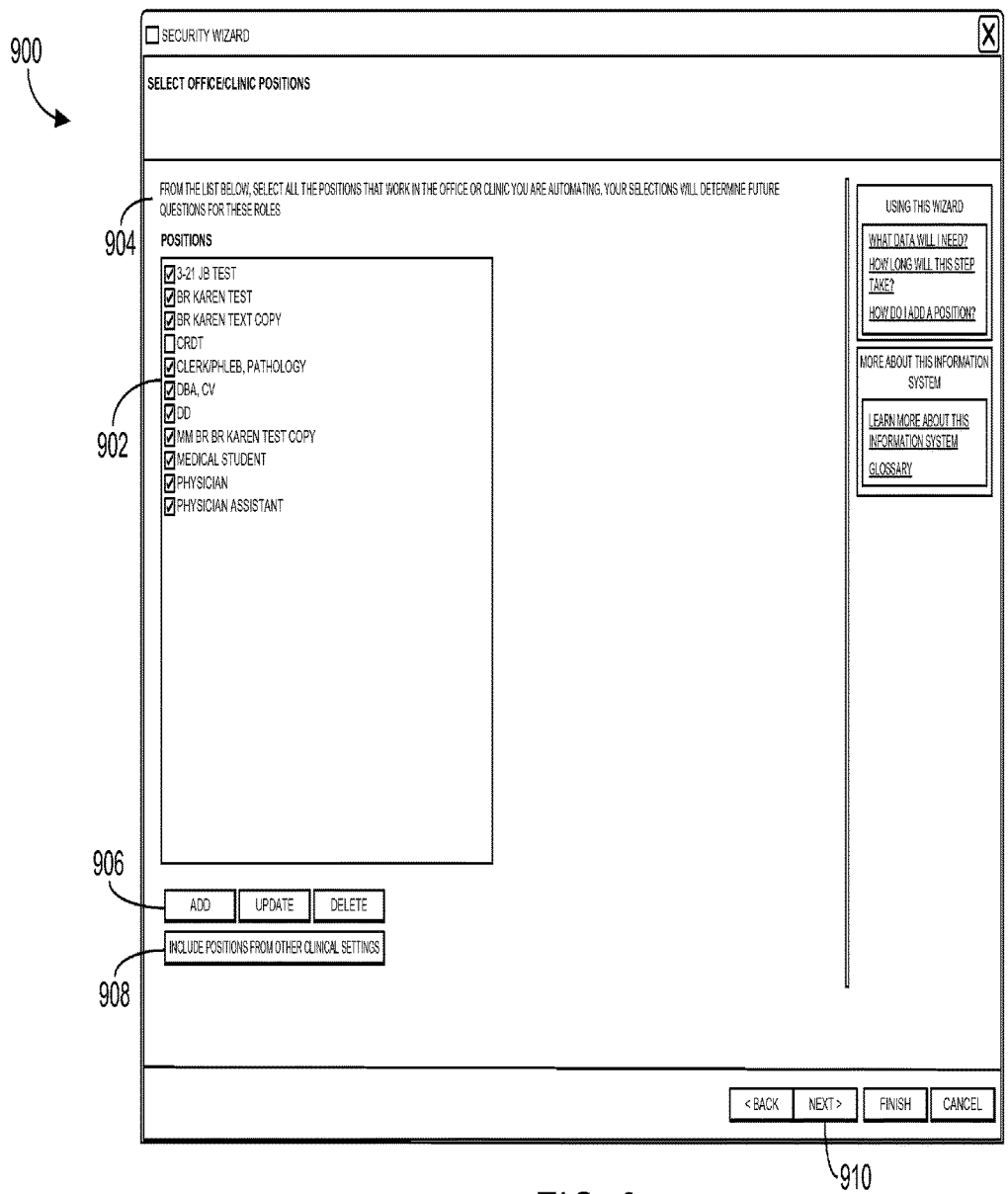
FIG. 9 is a screen display, in accordance with an embodiment of the present invention, illustrating a list of positions for which security may be configured in association with an office or clinic a user desires to automate.

Turning now to FIG. 9, an exemplary screen display illustrating a list of positions for which security may be configured in association with an office or clinic a user desires to automate is shown and designated generally as reference numeral 900. User interface 900 includes a positions for selection display portion 902 and an instructional display portion 904. The positions for selection display portion 902 is configured to display a list of positions for which security/privileges may be set for the healthcare information system being configured, implemented and/or maintained. The list of positions displayed may be derived, for instance, from pre-configured content component 218 and/or survey-learned data component 228 of system architecture 200 of FIG. 2. Additionally, if the user is updating the healthcare information system such that there is already an available list of positions specific to the user, for instance, from facility- and personnel-specific content component 212 of the system architecture 200 of FIG. 2, the list of displayed positions may be flexed accordingly.

The instructional display portion 904 is configured to display instructions which inform the user what tasks he is to complete with respect to user interface 900. In this regard, the instructional display portion 904 contains instructions informing the user "[f]rom the list below, [to] select all the positions that work in the office or clinic you are automating." The user is also informed that the selections made will determine future questions for these roles.

In practice, a user may select the check box displayed next to the name or designation for each position listed in the positions for selection display portion 902 that he desires to automate. If a position is desired that does not appear on the list, the user may select the selectable "Add" indicator 906 to free-text add a position or may select the selectable "Include Positions From Other Clinical Settings" indicator 908 to select additional positions from a different list of positions.

If the user hovers a pointer (e.g., a mouse pointer) over any of the positions listed in the positions for selection display portion 902, a text box (not shown) configured to display a description of what security privileges personnel in that position typically have may be displayed. (Such information may be derived, for instance, from pre-configured content component 218 and/or survey-learned data component 228 of system architecture 200 of FIG. 2.) In this way, if a user is unfamiliar with a particular position or acronym position designation, he may easily obtain assistance in figuring out what the name or designation is intended to represent.

Figure 10:
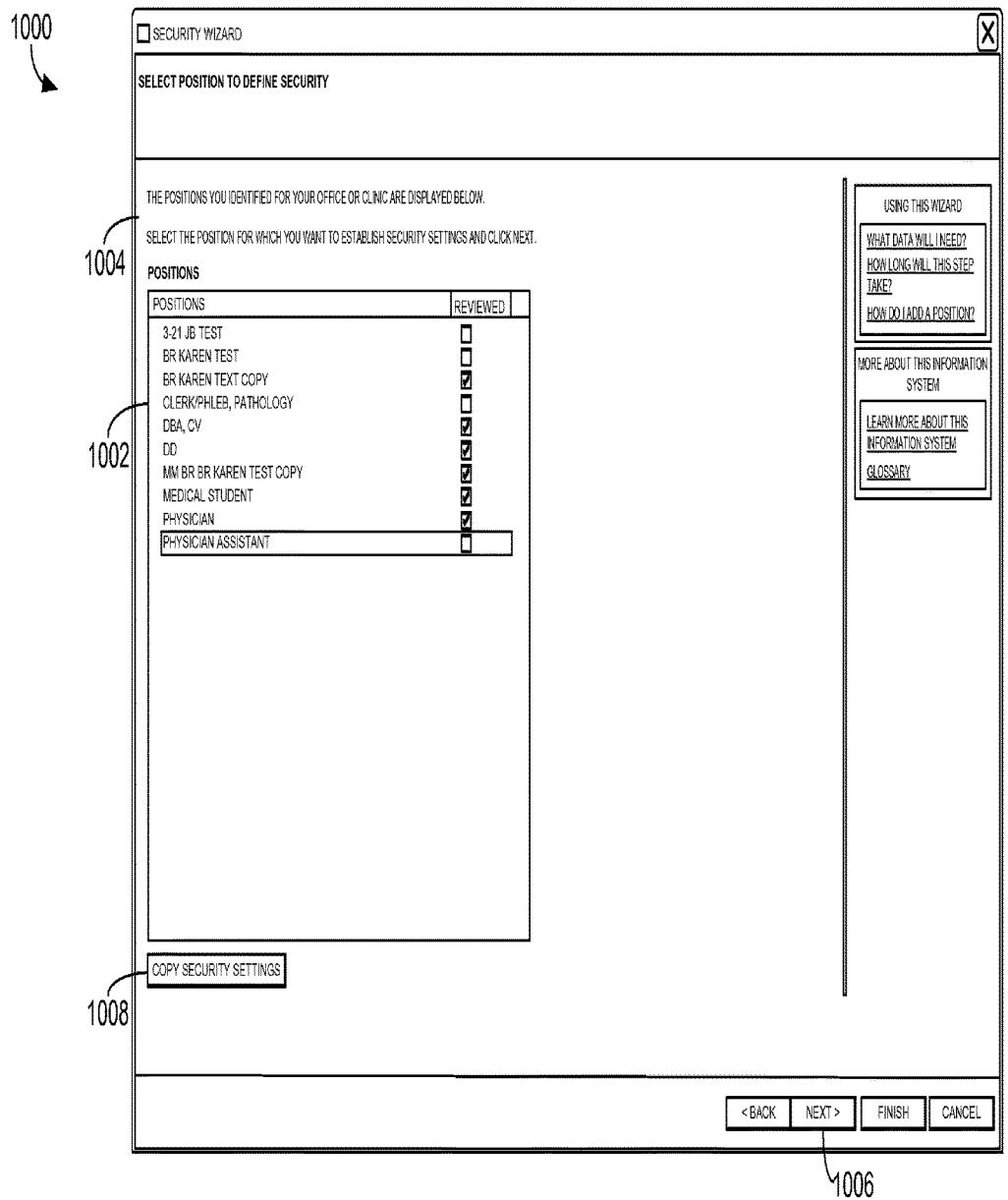
FIG. 10 is a screen display of an exemplary user interface illustrating a list of those positions that were selected in the screen display of FIG. 9, each position being selectable to initiate the defining of security pertinent thereto, in accordance with an embodiment of the present invention.

Once the user has selected each of the positions he desires to automate from the positions for selection display portion 902, he may select the selectable "Next" indicator 910. Upon such selection, the screen display of FIG. 10 may be displayed. In FIG. 10, an exemplary user interface illustrating a list of those positions that were selected in the screen display of FIG. 9, each position being selectable to initiate the defining of security pertinent thereto, is shown and designated generally as reference numeral 1000. User interface 1000 includes a selected positions display portion 1002 and an instructional display portion 1004 configured to display instructions which inform the user what tasks he is to complete with respect to user interface 1000. In this regard the instructional display portion 1004 informs the user that the positions he identified for the office or clinic being automated in FIG. 9 are shown and that he is to select one of the positions for which establishment of security settings is desired. Once the user has selected one of the positions from the list of positions displayed in the selected positions display portion 1002, he may select the selectable "Next" indicator 1006 to begin setting security/privileges for the selected position. In the illustrated example, the position of "Physician Assistant" has been selected.

It should be noted that user interface 1000 additionally includes a "Copy Security Settings" selectable indicator 1008. Selection of indicator 1008 will permit the user to copy security settings that have already been set with respect to one position to another position. In this way, significant time is saved in setting security settings for positions for which there is commonality and/or for which similar or identical privileges are desired.

Upon selection of the selectable "Next" indicator 1006 of user interface 1000, a series of screen displays prompting selection of privileges for the selected position are sequentially displayed. Initially, the screen display shown in FIG. 11 may be displayed. In FIG. 11, an exemplary user interface configured to permit a user to define position security with respect to viewing resource schedules, indicating arrival/location, allergies, problems and diagnosis, and procedures is shown and designated generally as reference numeral 1100. Once the user has selected the desired privileges displayed on user interface 1100, he may select the selectable "Next" indicator 1102 to continue with security/privileges designation.

Figure 12:
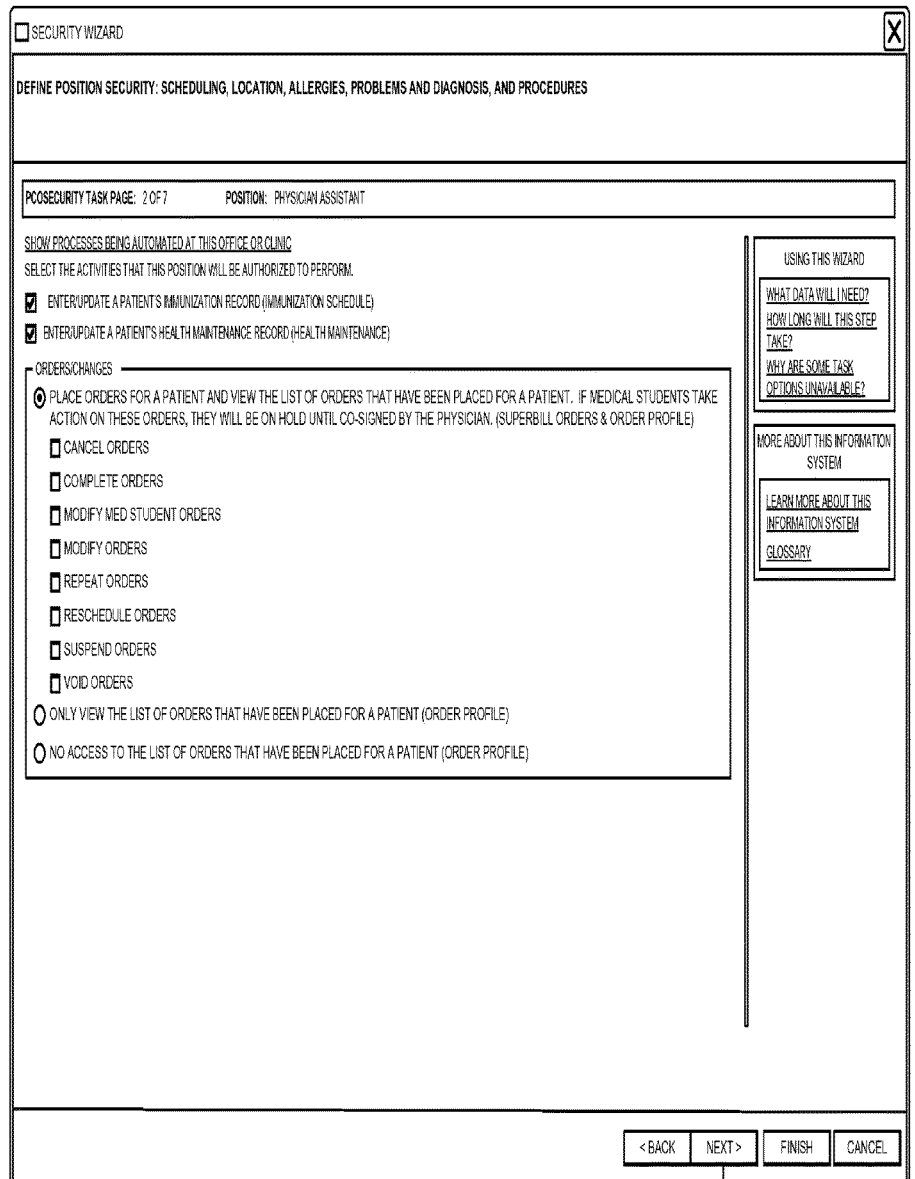
FIG. 12 is a screen display, in accordance with an embodiment of the present invention, of an exemplary user interface configured to permit a user to define position security with respect to immunization, health records, and orders and charges.

Upon selection of the selectable "Next" indicator 1102 of FIG. 11, the screen display shown in FIG. 12 may be displayed. In FIG. 12, an exemplary user interface configured to permit a user to define position security with respect to immunization records, health maintenance records, and orders and charges is shown and designated generally as reference numeral 1200. Once the user has selected the desired privileges displayed on user interface 1200, he may select the selectable "Next" indicator 1202 to continue with security/privileges designation.

Figure 13:
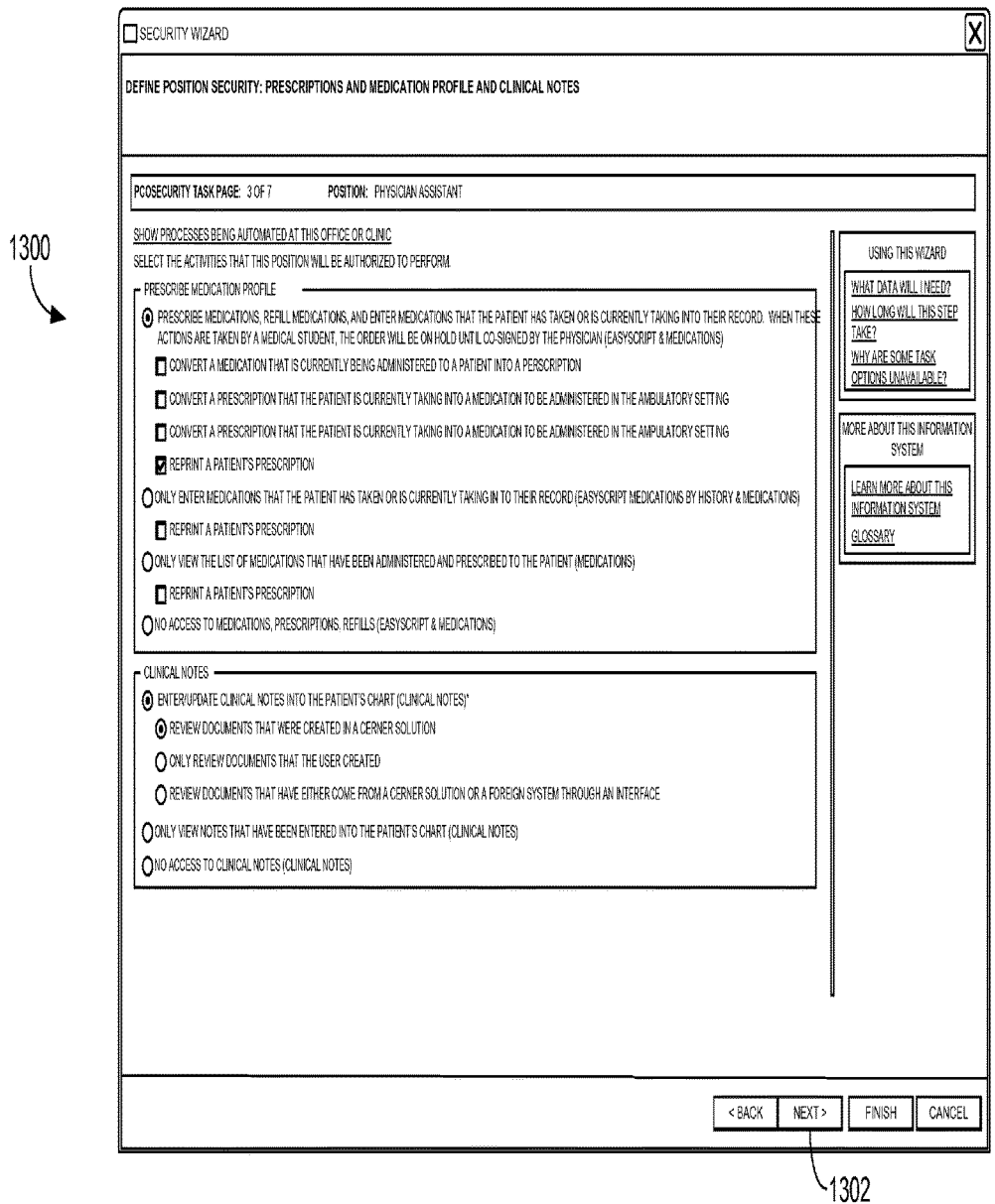
FIG. 13 is a screen display, in accordance with an embodiment of the present invention, of an exemplary user interface configured to permit a user to define position security with respect to prescriptions, medication profiles and clinical notes.

Upon selection of the selectable "Next" indicator 1202 of FIG. 12, the screen display shown in FIG. 13 may be displayed. In FIG. 13, an exemplary user interface configured to permit a user to define position security with respect to prescriptions and medication profile and clinical notes is illustrated and designated generally as reference numeral 1300. Once the user has selected the desired privileges displayed on user interface 1300, he may select the selectable "Next" indicator 1302 to continue with security/privileges designation.

Figure 14:
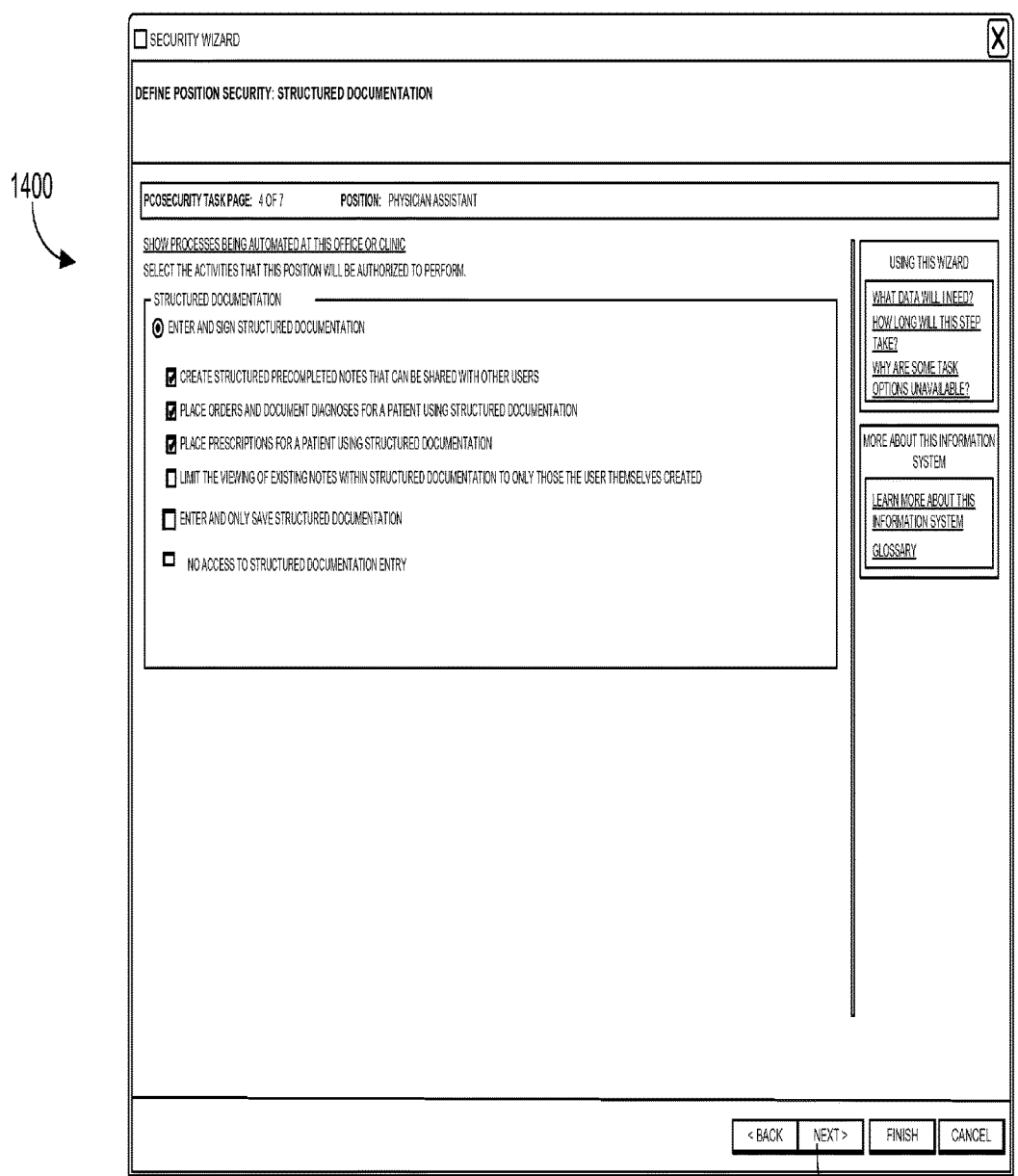
FIG. 14 is a screen display, in accordance with an embodiment of the present invention, of an exemplary user interface configured to permit a user to define position security with respect to structured documentation.

Upon selection of the selectable "Next" indicator 1302 of FIG. 13, the screen display shown in FIG. 14 may be displayed. In FIG. 14, an exemplary user interface configured to permit a user to define position security with respect to structured documentation is illustrated and designated generally as reference numeral 1400. Once the user has selected the desired privileges displayed on user interface 1400, he may select the selectable "Next" indicator 1402 to continue with security/privileges designation.

Upon selection of the selectable "Next" indicator 1402 of FIG. 14, the screen display shown in FIG. 15 may be displayed. In FIG. 15, an exemplary user interface configured to permit a user to define position security with respect to forms, pediatric growth chart, patient history, and viewing/commenting on patient results is illustrated and designated generally as reference numeral 1500. Once the user has selected the desired privileges displayed on user interface 1500, he may select the selectable "Next" indicator 1502 to continue with security/privileges designation.

Figure 16:
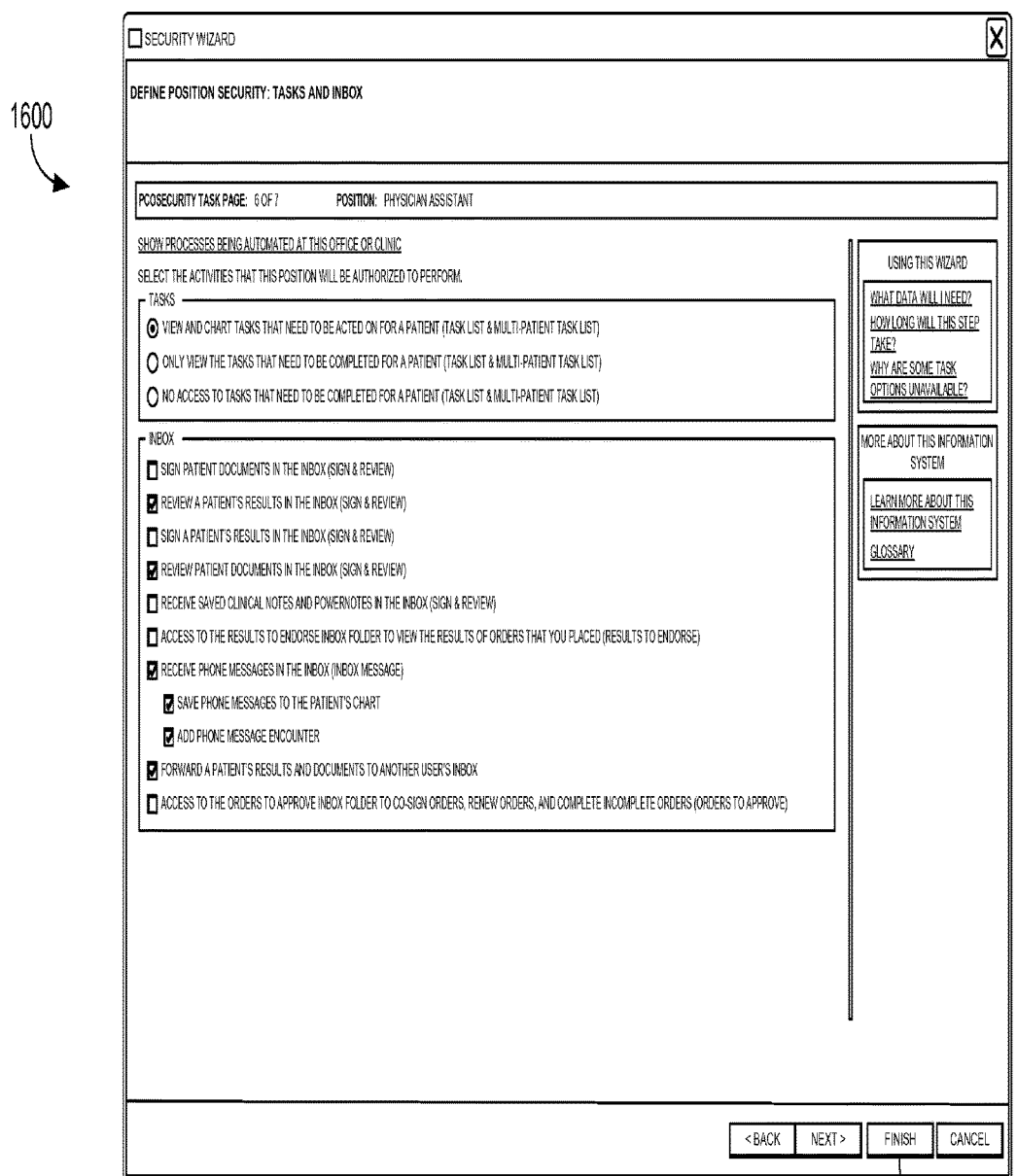
FIG. 16 is a screen display, in accordance with an embodiment of the present invention, of an exemplary user interface configured to permit a user to define position security with respect to tasks and inbox.

Upon selection of the selectable "Next" indicator 1502 of FIG. 15, the screen display shown in FIG. 16 may be displayed. In FIG. 16, an exemplary user interface configured to permit a user to define position security with respect to tasks and inbox is illustrated and designated generally as reference numeral 1600. Once the user has selected the desired privileges displayed on user interface 1600, he may select the selectable "Next" indicator 1602 to continue with security/privileges designation.

Figure 17:
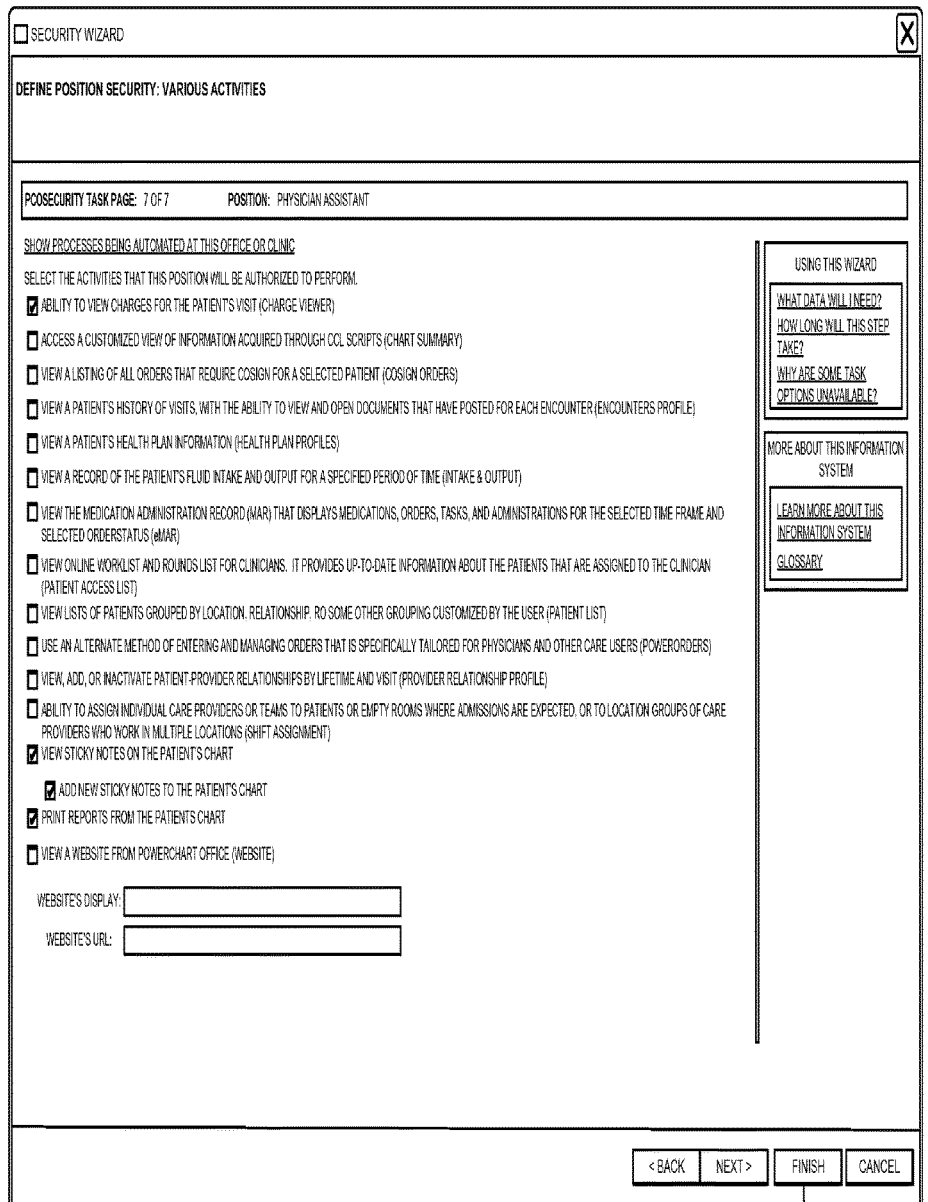
FIG. 17 is a screen display, in accordance with an embodiment of the present invention, of an exemplary user interface configured to permit a user to define position security with respect to various activities.
Figure 18:
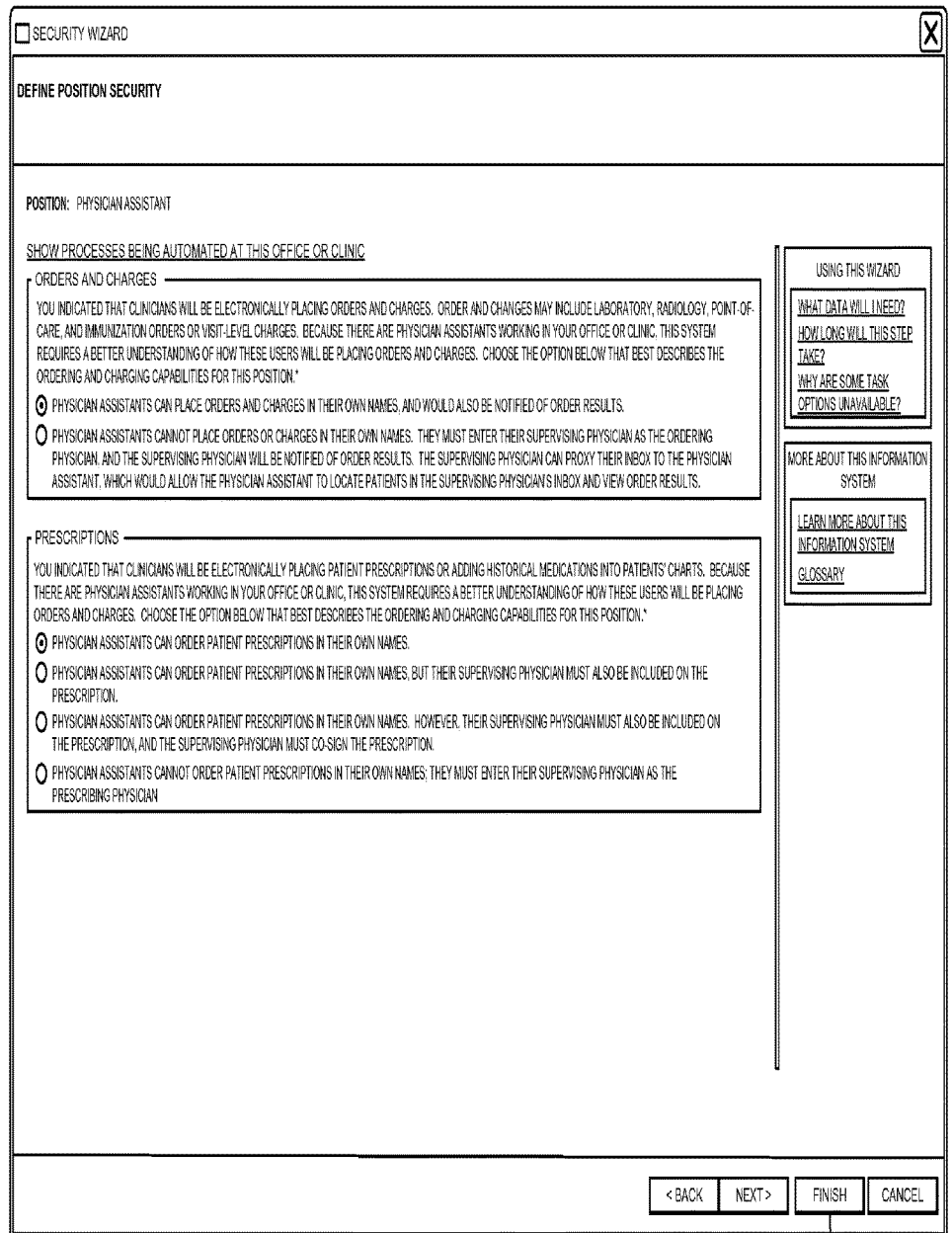
FIG. 18 is a screen display, in accordance with an embodiment of the present invention, that may be displayed upon user selection of security settings that require further clarification.
Figure 19:
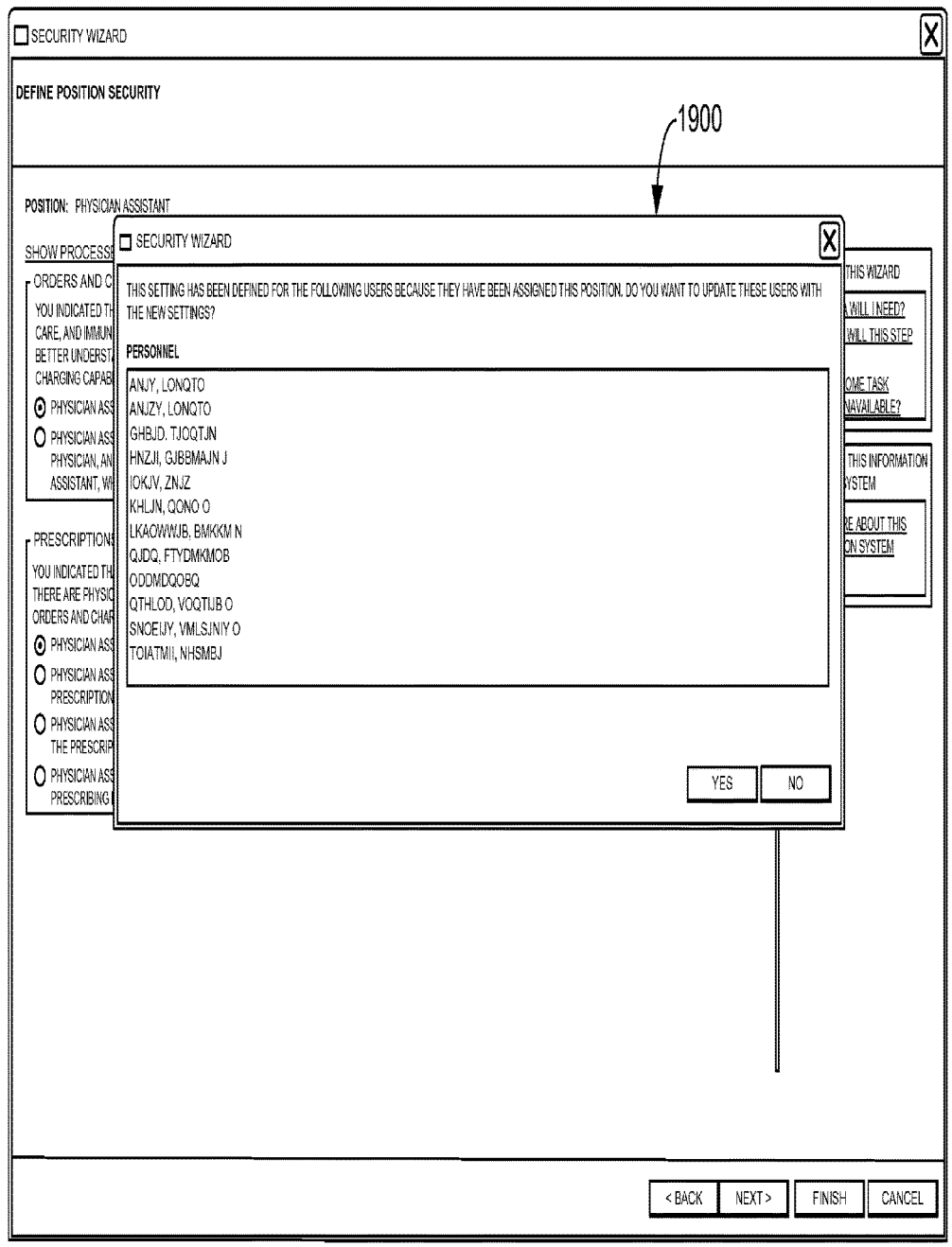
FIG. 19 is a screen display, in accordance with an embodiment of the present invention, that may be displayed upon selection of the ""Finish" selectable indicator of FIG. 18 illustrating a list of personnel that have been assigned to the position for which security has been set that provides the user with the opportunity to update or not update each member of the list in accordance with the security settings.
Figure 20:
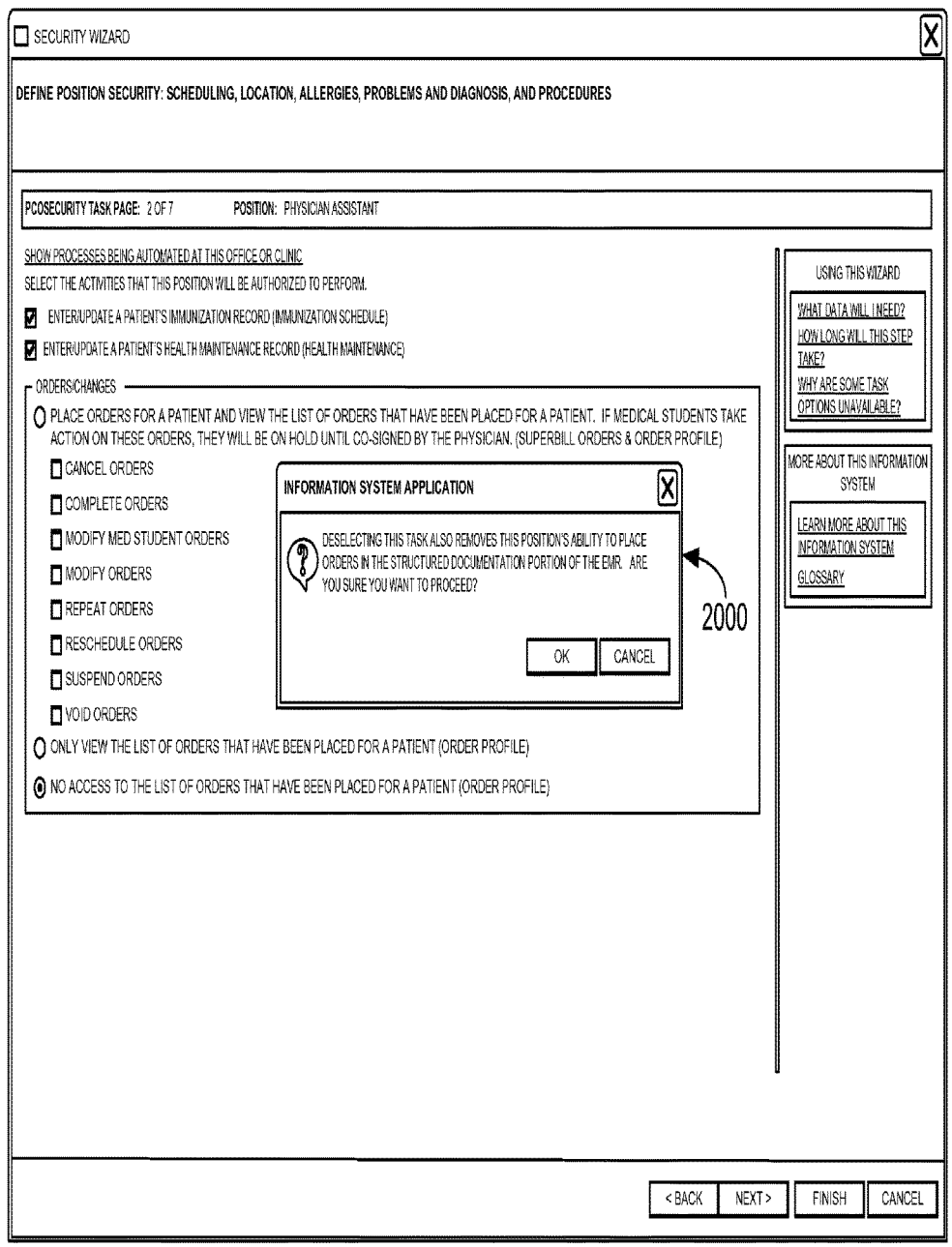
FIG. 20 is a screen display illustrating an alert that may be displayed upon user selection or de-selection of a security setting that is at odds with another security setting, in accordance with an embodiment of the present invention.

Upon selection of the selectable "Next" indicator 1602 of FIG. 16, the screen display shown in FIG. 17 may be displayed. In FIG. 17, an exemplary user interface configured to permit a user to define position security with respect to various activities is illustrated and designated generally as reference numeral 1700. Once the user has selected the desired privileges displayed on user interface 1700, he may select the selectable "Next" indicator 1702 to continue with security/privileges designation. At this point, the user has completed designation of security/privileges but one or more of the selected privileges may require clarification. If this is the case, one or more user interfaces may be displayed upon selection of the selectable "Next" indicator 1702 of FIG. 17 that prompt the required clarification. One such exemplary screen display is shown in FIG. 18. It should be noted that if no privileges have been selected that require clarification, selection of the selectable "Next" indicator 1702 of FIG. 17 may instead initiate display of the screen display of FIG. 19. FIG. 19 is more fully described herein below.

Note that if the user is updating the healthcare information system such that there is already available information pertaining to the security/privileges available to personnel designated to certain positions that is specific to the user, for instance, from facility- and personnel-specific content component 212 of the system architecture 200 of FIG. 2, such selections may be defaulted for any of the screen displays of FIGS. 11-17. Even if such information is defaulted, however, the user may still be provided with the option to change the previously designated security/privileges for each position.

As previously stated, if clarification of security/privileges is required, one or more user interfaces may be displayed upon selection of the selectable "Next" indicator 1702 of FIG. 17 that prompt the required clarification. FIG. 18 shows one example of a clarification user interface, such interface being designated generally as reference numeral 1800. Note that the clarification prompts displayed on user interface 1800 are customized and relevant to the illustrated selections made in FIGS. 11-17. That is, any clarification user interfaces that are displayed will be flexed based on the previous security designations. As such, it will be understood and appreciated by those of ordinary skill in the art that user interface 1800 is merely exemplary. Once all clarification prompts displayed on user interface 1800 have been addressed, the user may select the selectable "Finish" indicator 1802 to indicate that setting of security/privileges is complete.

Upon selection of the selectable "Finish" indicator 1802 of FIG. 18, or if no clarification is required subsequent to user selection of the selectable "Next" indicator 1702 of FIG. 17, the screen display of FIG. 19 may be displayed. In FIG. 19, an exemplary user interface illustrating a list of personnel that have been assigned to the position for which security has been set is shown and designated generally as reference numeral 1900. User interface 1900 provides the user with the opportunity to update or not update each member of the list in accordance with the previously designated security settings. The user may select each of the names on the displayed personnel list and indicate whether or not he would like the security settings to be updated for that particular individual in accordance with the designated security settings. Once the user has indicated "yes" or "no" with respect to each individual, the defining of security/privileges for that position is complete. The user may subsequently again initiate the process to define security/privileges for another position. Alternatively, a screen display (not shown) may be displayed prompting the user to select another position for which to define security or affirmatively state that he is finished with the security designation task. Any and all such variations are contemplated to be within the scope of embodiments of the present invention.

Embodiments of the present invention provide the user with alerts or indicators if the user selects or de-selects a security/privilege option that creates an inconsistency with other tasks the personnel assigned to that position designation may be set to be able to perform. For instance, with reference to FIG. 20, a screen display illustrating an alert that may be displayed upon user selection or de-selection of a security/privilege setting that is at odds with another security/privilege setting is illustrated and designated generally as reference numeral 2000. In the illustrated embodiment, suppose the user has previously indicated that personnel categorized as Physician Assistants are to have the ability to place orders in a physician's notation portion of a patient's electronic medical record. Subsequently, and in accordance with this prior designation, upon displaying the screen display wherein security with respect to orders and charges is to be specified (e.g., screen display 1200 of FIG. 12), the selection which indicates that that Physician Assistants are to be able to place orders for a patient and view the list of orders that have been placed for a patient may be selected as a default. If the user de-selects this option, the alert 2000 may be displayed informing the user that de-selecting that particular task will also change the previously designated security/privilege setting. The user may then be asked to affirmatively state whether this is his intent before he is allowed to proceed. In this way, inconsistencies in the security/privileges being set throughout the security process are flagged and reconciled prior to completion. Additionally, based on the user's selections during the conflict reconciliation process, indications of selection or de-selection of prior presented options may change. That is, if the user were to scroll back through previously completed screen displays, one or more options may appear changed from the selection(s) initially made by the user, the changed selection(s) being in accordance with the user's selections during the conflict reconciliation process.

Figure 21:
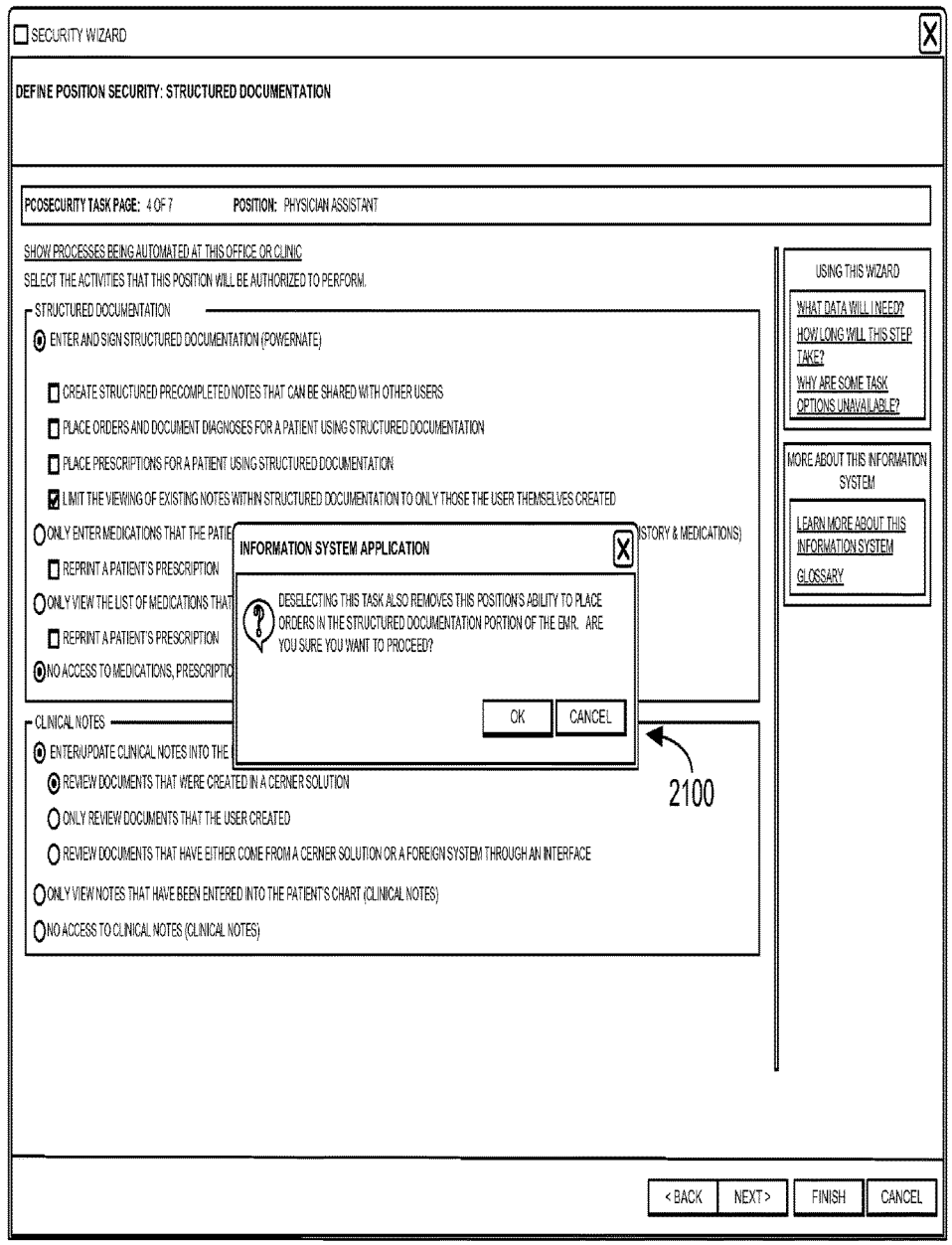
FIG. 21 is a screen display illustrating an alert that may be displayed upon user selection or de-selection of a security setting that is at odds with another security setting, in accordance with an embodiment of the present invention.

FIG. 21 illustrates another example of the above-described conflict reconciliation functionality. In FIG. 21, a screen display illustrating an alert that may be displayed upon user selection or de-selection of a security setting that is at odds with another security setting is shown and designated generally as reference numeral 2100. In the illustrated embodiment, suppose the user has previously indicated that personnel categorized as Physician Assistants are to have the ability to order prescriptions in a physician's notation portion of a patient's electronic medical record. Subsequently, and in accordance with this prior designation, upon displaying the screen display wherein security with respect to prescriptions and the patient's medication profile is to be specified (e.g., screen display 1300 of FIG. 13), the selection which indicates that that Physician Assistants are to be able to prescribe medications, refill medications, and enter medications that the patient has taken or is currently taking into their record may be selected as a default. If the user de-selects this option, the alert 2100 may be displayed informing the user that de-selecting that particular task will also change the previously designated security/privilege setting. The user may then be asked to affirmatively state whether this is his intent before he is allowed to proceed.

From the perspective of workflows in a clinical setting, there are certain tasks that if an individual having a particular position designation is permitted to participate in, it stands to reason that there are other tasks in which he should also be able to participate. Such corresponding "reasonable" tasks may be derived, for instance, from pre-configured content component 218 of the system architecture 200 of FIG. 2, such content including survey-learned data. For instance, if an individual having a particular position designation is permitted to update a patient's allergy profile, that same individual should also be able to view that patient's allergy profile. In such circumstances, embodiments of the present invention may provide an alert to the user asking for the user to either verify or synchronize any apparent inconsistencies. A screen display illustrating an alert that may be displayed upon user selection or de-selection of a security/privilege setting that creates an apparent inconsistency is illustrated in FIG. 22.

Figure 22:
FIG. 22 is a screen display, in accordance with an embodiment of the present invention, that may be displayed upon user selection of security privileges that reasonably may be out of synch with one another permitting the user to change or verify such selections.

FIG. 22 shows a screen display that may be displayed upon user selection of security privileges that reasonably may be out of synch with one another, such screen display being designated generally as reference numeral 2200. In the illustrated embodiment, the user has indicated that personnel assigned to the positions "BR Karen Test", "Reg Clerk", and "Tech, Cytology" are to have view and update privileges that are inconsistent with one another. Accordingly, the user is asked to either synchronize the privileges according to the previously set view privileges or update privileges, or to affirmatively indicate that he intends the privileges to remain out of synch. To synchronize the privileges, the user may select each of the positions and indicate the privileges he intends personnel assigned to the selected position to have. When the user has completed the synchronization, he may select the selectable "OK" indicator 2202 to indicate that the task has been completed.

Each of the security/privilege selections made by a user utilizing the security selection process according to embodiments of the present invention may have one or more effects concerning the options with which personnel assigned to the pertinent clinical setting position may be presented. By way of example, turning to FIGS. 23-30, a series of exemplary screen displays are provided illustrating a plurality of end-user effects selection or de-selection of a particular security/privilege option in the security selection process described herein above with reference to FIGS. 8-22 may have. It will be understood and appreciated by those of ordinary skill in the art that the screen displays presented in FIGS. 23-30 are exemplary in nature and are not intended to limit the scope of the invention in any way.

Figure 23:
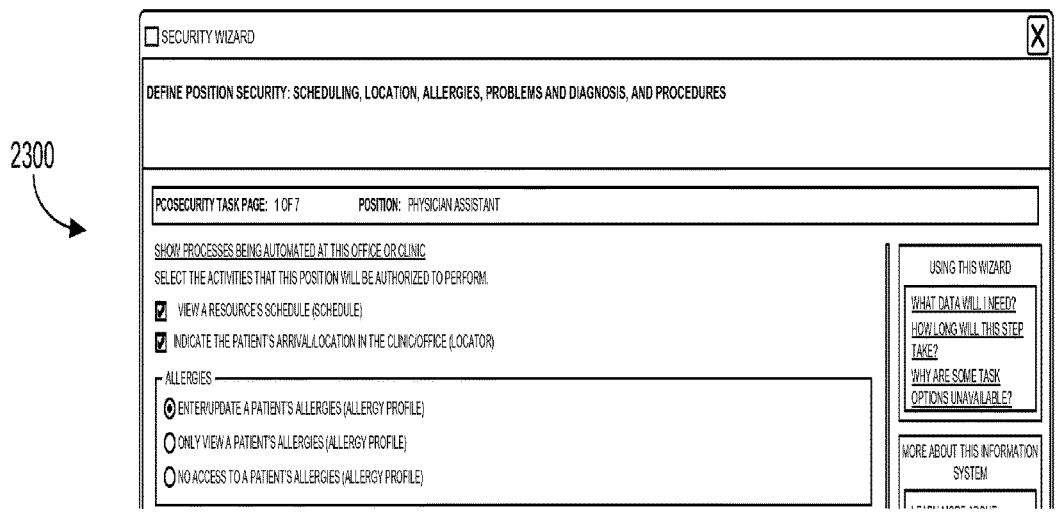
FIG. 23 is a partial screen display, in accordance with an embodiment of the present invention, of an exemplary user interface configured to permit a user to define position security with respect to allergies, wherein the option entitled "Enter/Update a patient's allergies (Allergy Profile)" has been selected.
Figure 24:
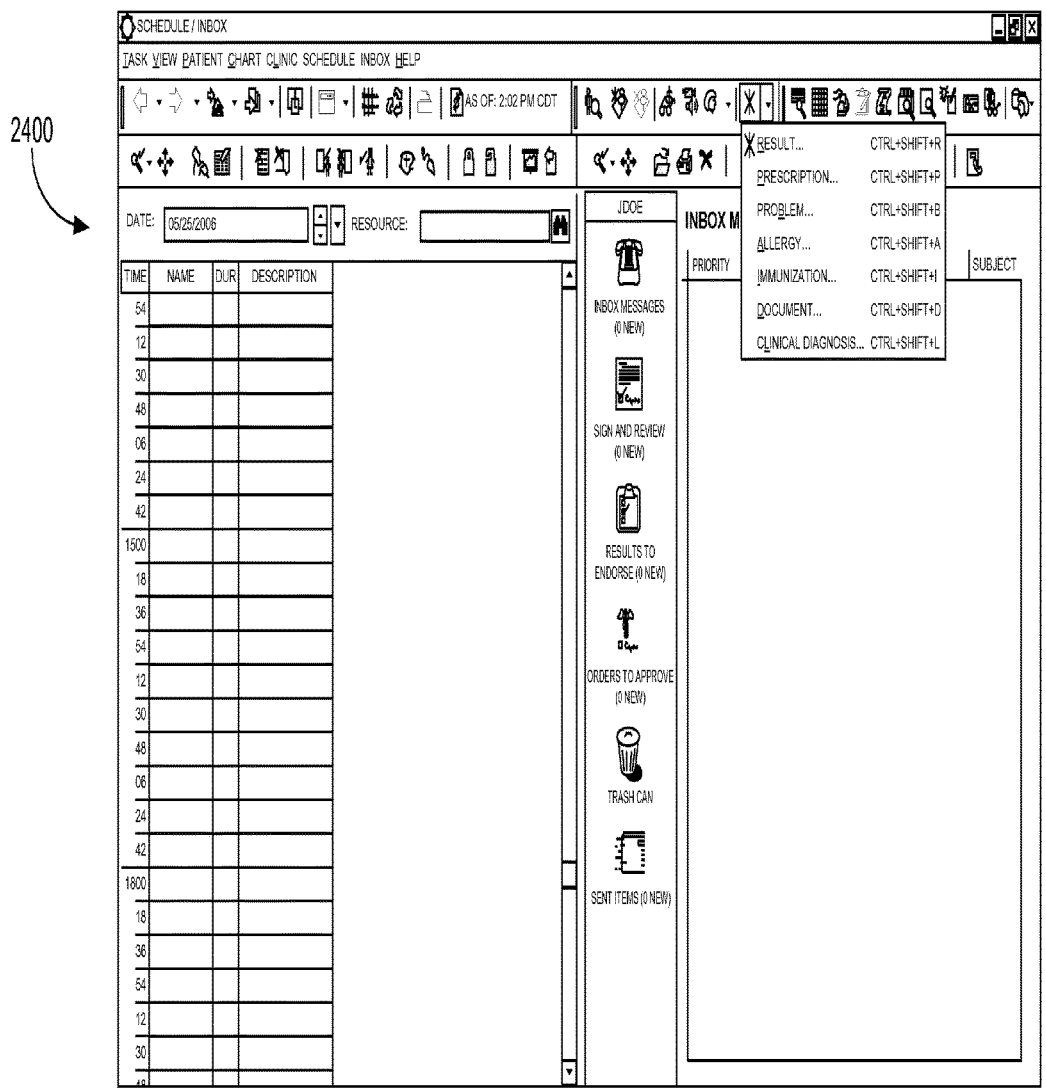
FIG. 24 is a screen display, in accordance with an embodiment of the present invention, illustrating the effect selection of the "Enter/Update a patient's allergies (Allergy Profile)" option of FIG. 23 may have on the options available to an end-user of the healthcare information system being configured, implemented and/or maintained.
Figure 25:
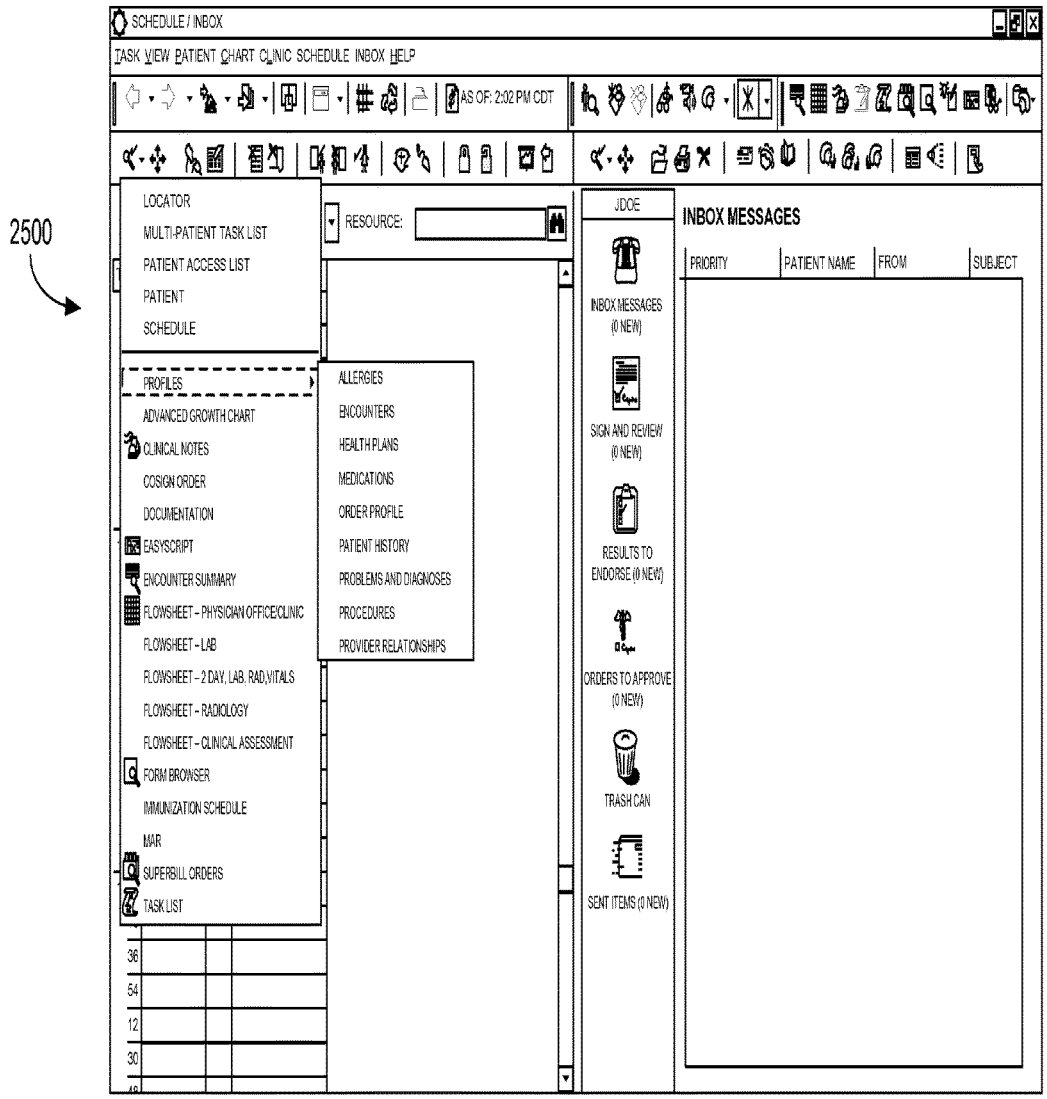
FIG. 25 is a screen display, in accordance with an embodiment of the present invention, illustrating the effect selection of the "Enter/Update a patient's allergies (Allergy Profile)" option of FIG. 23 may have on the options available to an end-user of the healthcare information system being configured, implemented and/or maintained.
Figure 26:
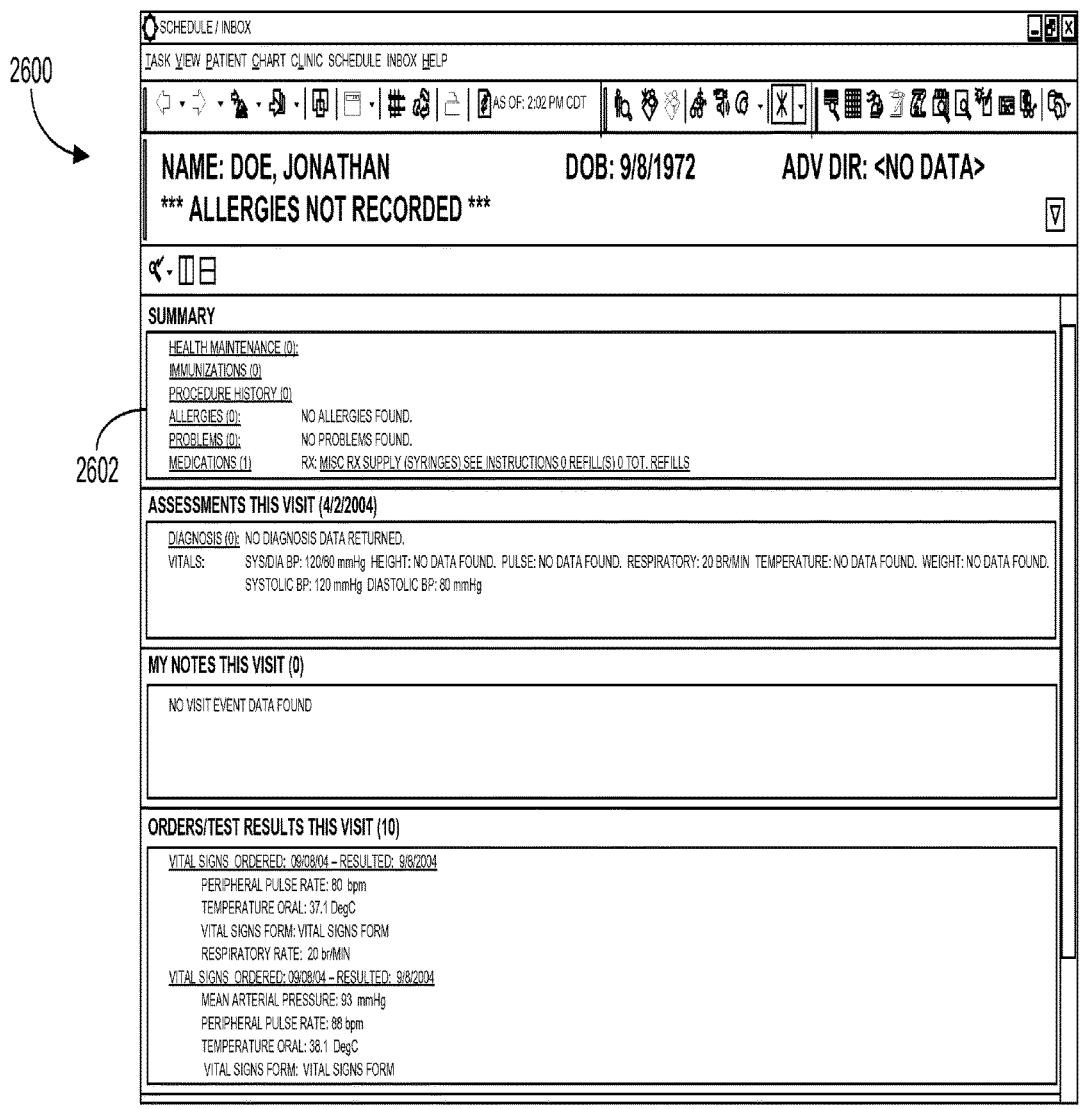
FIG. 26 is a screen display, in accordance with an embodiment of the present invention, illustrating the effect selection of the "Enter/Update a patient's allergies (Allergy Profile)" option of FIG. 23 may have on the options available to an end-user of the healthcare information system being configured, implemented and/or maintained.
Figure 27:
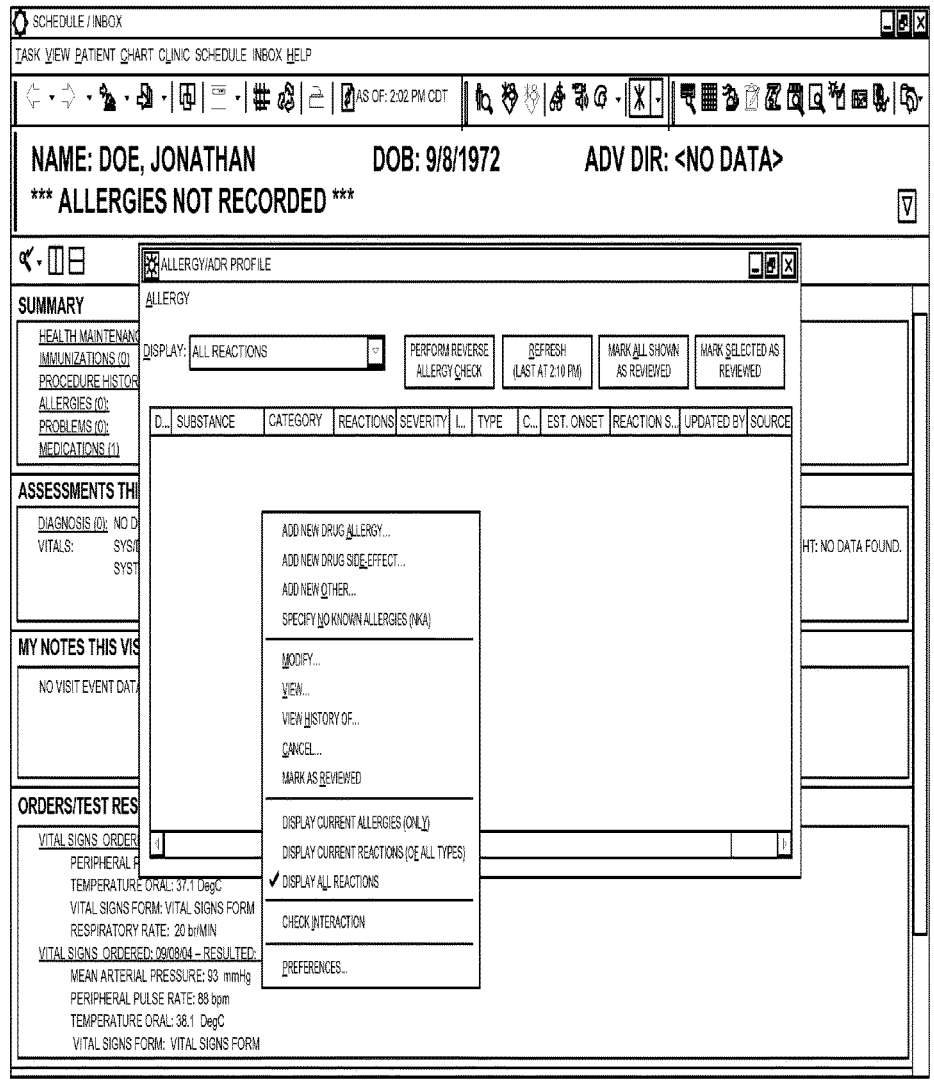
FIG. 27 is a screen display, in accordance with an embodiment of the present invention, illustrating the effect selection of the "Enter/Update a patient's allergies (Allergy Profile)" option of FIG. 23 may have on the options available to an end-user of the healthcare information system being configured, implemented and/or maintained.

With initial reference to FIG. 23, a partial screen display of an exemplary user interface configured to permit a user to define position security with respect to allergies, wherein the option entitled "Enter/Update a patient's allergies (Allergy Profile)" has been selected with respect to personnel assigned to the category of Physician Assistant is illustrated and designated generally as reference numeral 2300. When this option is selected, each of the screen displays shown in FIGS. 24-27 may be displayed to an individual assigned to the category of Physician Assistant when navigating through a patient's electronic medical record. As can be seen, the option of "Allergy" is presented to the end-user in screen display 2400 of FIG. 24 and the end-user is presented with the option to view the allergy profile of the patient in the screen display 2500 of FIG. 25. If the user elects in the screen display 2500 of FIG. 25 to view the patient's allergy profile, the screen display 2600 of FIG. 26 illustrating a patient's allergy profile may be displayed. In this instance, no allergies have been recorded in the patient's allergy profile. Upon selection of the "Allergies (0):" selectable link from the Summary display portion 2602 of the screen display 2600 of FIG. 26, the screen display 2700 of FIG. 27 may be displayed, wherein the end-user is permitted to select an option to add a new drug allergy to the patient's allergy profile.

Figure 28:
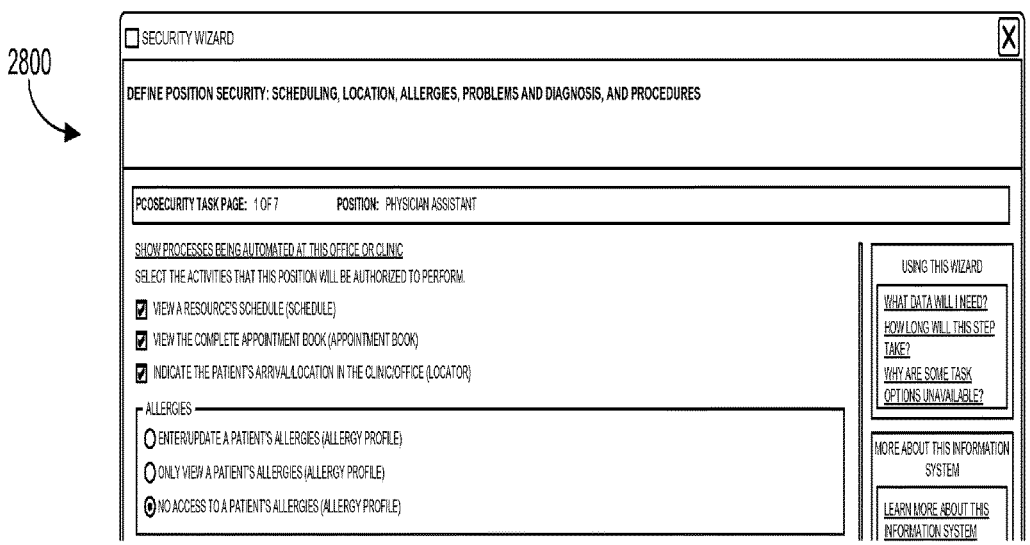
FIG. 28 is a partial screen display, in accordance with an embodiment of the present invention, of an exemplary user interface configured to permit a user to define position security with respect to allergies, wherein the option entitled "No access to a patient's allergies (Allergy Profile)" has been selected.
Figure 29:
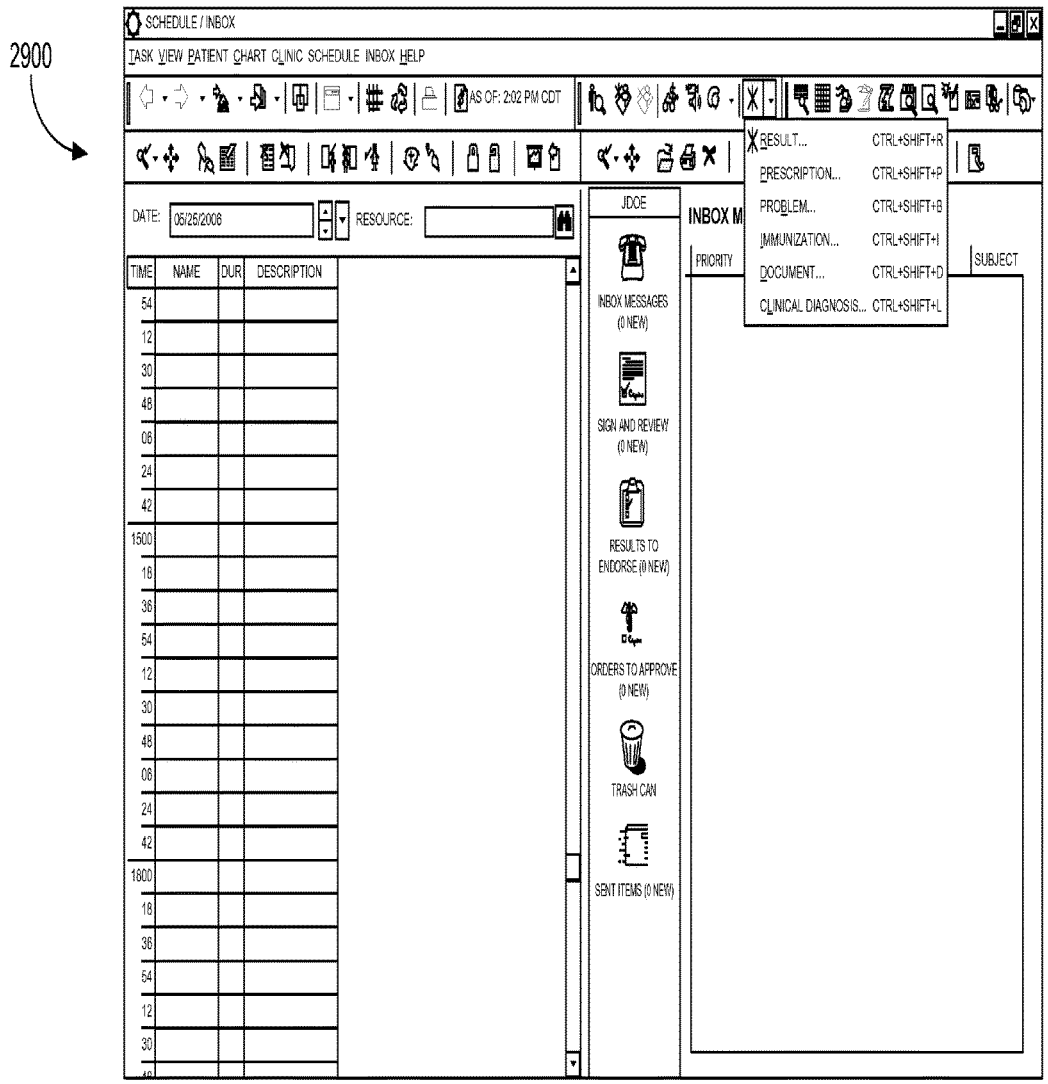
FIG. 29 is a screen display, in accordance with an embodiment of the present invention, illustrating the effect selection of the "No access to a patient's allergies (Allergy Profile)" option of FIG. 28 may have on the options available to an end-user of the healthcare information system being configured, implemented and/or maintained.
Figure 30:
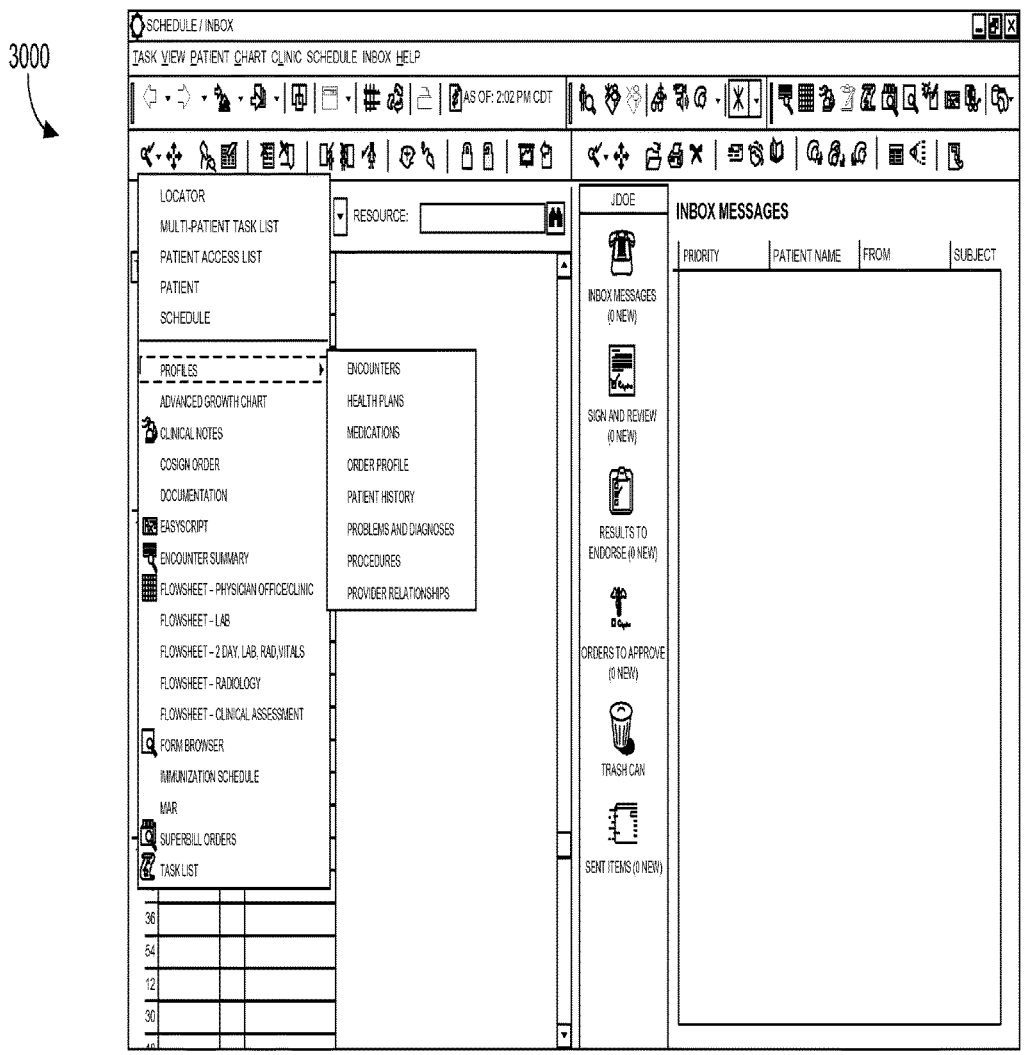
FIG. 30 is a screen display, in accordance with an embodiment of the present invention, illustrating the effect selection of the "No access to a patient's allergies (Allergy Profile)" option of FIG. 28 may have on the options available to an end-user of the healthcare information system being configured, implemented and/or maintained.

By way of contrast, the screen displays of FIGS. 28-30 illustrate the difference in each of the above-described screen displays if the "Enter/Update a patient's allergies (Allergy Profile" security/privilege option of the screen display 2300 of FIG. 23 had not been selected. In this regard, in FIG. 28 a partial screen display of an exemplary user interface configured to permit a user to define position security with respect to allergies, wherein the option entitled "Enter/Update a patient's allergies (Allergy Profile)" has not been selected with respect to personnel assigned to the category of Physician Assistant is illustrated and designated generally as reference numeral 2800. When this option is not selected, each of the screen displays shown in FIGS. 29 and 30 may be displayed to an individual assigned to the category of Physician Assistant when navigating through a patient's electronic medical record. As can be seen with reference to the screen display 2900 of FIG. 29, though the option of "Allergy" was presented to the end-user when the "Enter/Update a patient's allergies (Allergy Profile)" security privilege option was selected (FIG. 24), such is not only not available but not even displayed when the option is not selected. Similarly, with reference to the screen display 3000 of FIG. 30, when the "Enter/Update a patient's allergies (Allergy Profile)" security/privilege option is not selected, the end-user is not presented with the option to view the allergy profile of the patient. (Contrast this with the screen display 2500 of FIG. 25 that may be displayed when the "Enter/Update a patient's allergies (Allergy Profile)" security/privilege option is selected.) As the end-user is not allowed to view the patient's allergy profile, the screen displays 2600 and 2700 of FIGS. 26 and 27, respectively, are not presented to the end-user.

As can be understood, the present invention provides systems, methods, and computer-readable media having computer-executable instructions embodied thereon for configuration, implementation and/or maintenance of a healthcare information system. Such configuration, implementation and/or maintenance may include building of a healthcare information system from the ground level or modifying or converting an existing healthcare information system. Utilizing the systems, methods, and computer-readable media herein described, security/privilege conflicts are minimized as such inconsistencies are flagged and reconciliation is attempted prior to completion of the configuration, implementation and/or maintenance process. Additionally, as information is gleaned from a series of customized, pointed questions, and items for a user to elect to select or de-select rather than from free-text information entry, elements that don't make sense from a clinical perspective are minimized as well. For instance, entry of a diagnosis of penicillin (which doesn't make sense from a clinical perspective) would not be allowed.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

What is claimed is:

1. A system for building a customized healthcare information system, the system comprising:
   an existing healthcare information system associated with a healthcare facility;
   a preconfigured content component; and
   a survey component in communication with a graphical user interface (GUI), the survey component comprising at least one processor and one or more non-transitory computer-readable media having computer-executable instructions embodied thereon that, when executed, cause the at least one processor to perform a method comprising:
   mining the existing healthcare information system associated with the healthcare facility for information related to a portion of the customized healthcare information system to be built;
   formatting and inputting the mined information to requirements of the survey component;
   seeding, from the preconfigured content component, the mined information with preconfigured healthcare information derived from a preconfigured healthcare information system;
   presenting a series of screen displays to the user via the GUI, the series of screen displays having options for at least one of the mined information and the preconfigured healthcare information, wherein the series of screen displays is customized to the user based on a phase of configuration being performed by the user as determined by a user profile;
   building the portion of the customized healthcare information system by configuring the portion of the customized healthcare information system from preferences selected from the series of screen displays, wherein further building the portion of the customized healthcare information system comprises storing survey-learned data comprising the preferences selected from the series of screen displays; and reconfiguring the built portion of the customized healthcare information system by mining the stored survey-learned data, the mined survey-learned data being used to customize a second series of screen displays, wherein reconfiguration of the built portion of the customized healthcare information system is performed based on the second series of screen displays from the mined survey-learned data.

2. The system of claim 1, further comprising receiving an indication from the user associated with the existing healthcare facility that the user desires to build at least the portion of the customized healthcare information system.

3. The system of claim 1, further comprising surveying an existing system architecture to determine whether the existing healthcare information system is present.

4. The system of claim 1, further comprising a knowledge portal configured to provide informational assistance to the user.

5. The system of claim 4, wherein the knowledge portal converts technical language from technical support documents into a natural language format to provide the informational assistance to the user.

6. The system of claim 1, wherein the series of screen displays is configured to receive, as part of the input, additional information from the user.

7. The system of claim 1, wherein the preconfigured healthcare information system is at least based in part on regulations of a particular region.

8. The system of claim 1, wherein the series of screen displays presents a selectable option to the user, the selectable option comprising an option based on information mined from the existing healthcare information system, an option based on information derived from the preconfigured healthcare information system, and an option to enter new information.

9. One or more non-transitory computer-readable media having computer-executable instructions embodied thereon that, when executed, cause a processor to perform a method for building a portion of a customized healthcare information system, the method comprising:

mining an existing healthcare information system for information related to the portion of the customized healthcare information system to be built;

seeding the mined information in a survey component with preconfigured healthcare information related to the portion of the customized healthcare information system to be built;

presenting to a user a series of screen displays having options for at least one of the mined information and the preconfigured healthcare information, wherein the series of screen displays is customized to the user based on a phase of configuration being performed by the user as determined by a user profile;

building the portion of the customized healthcare information system by configuring the portion of the customized healthcare information system from preferences selected from the series of screen displays, wherein further building the portion of the customized healthcare information system comprises storing survey-learned data comprising the preferences selected from the series of screen displays; and reconfiguring the built portion of the customized healthcare information system by mining the stored survey-learned data, the mined survey-learned data being used to customize a second series of screen displays, wherein reconfiguration of the built portion of the customized healthcare information system is performed based on the second series of screen displays from the mined survey-learned data.

10. The media of claim 9, further comprising receiving an indication from the user, wherein the indication indicates that the user desires to configure the portion the customized healthcare information system.

11. The media of claim 9, further comprising surveying an existing system architecture to determine whether the existing healthcare information system is present.

12. The media of claim 9, further comprising formatting the mined information to requirements of the survey component.

13. The media of claim 9, wherein the preconfigured healthcare information is based in part on regulations of a particular healthcare system.

14. The media of claim 9, wherein the preconfigured healthcare information is based in part on a typical healthcare information system having typical healthcare information system preferences.

15. The media of claim 14, wherein the typical healthcare information system preferences are comprised in part on the survey-learned data.

16. The media of claim 9, wherein the series of screen displays is flexed based upon information in the survey component.

17. A computer implemented method performed by at least one computer processor, the method comprising:

mining an existing healthcare information system for existing information related to a portion of a customized healthcare information system to be built;

formatting and inputting the mined existing information into a survey component;

seeding, at the survey component, the mined existing information with preconfigured healthcare information related to the portion of the customized healthcare information system to be built;

presenting to a user a series of screen displays having options for at least one of the mined information and the preconfigured healthcare information, wherein the series of screen displays is customized to the user based on a phase of configuration being performed by the user as determined by a user profile;

building the portion of the customized healthcare information system by configuring the portion of the customized healthcare information system based on a preference selected from the series of screen displays, wherein further building the portion of the customized healthcare information system comprises storing survey-learned data comprising the preference selected from the series of screen displays; and reconfiguring the built portion of the customized healthcare information system by mining the stored survey-learned data, the mined survey-learned data being used to customize a second series of screen displays, wherein reconfiguration of the built portion of the customized healthcare information system is performed based on the second series of screen displays from the mined survey-learned data.

* * * * *